US008945831B2

(12) United States Patent
Whiteley

(10) Patent No.: US 8,945,831 B2
(45) Date of Patent: Feb. 3, 2015

(54) COMPOSITIONS AND METHODS FOR DETECTING JUVENILE RENAL DYSPLASIA OR CALCIUM OXALATE STONES IN DOGS

(75) Inventor: Mary Helen Whiteley, Peterborough (CA)

(73) Assignee: DOGenes Inc., Peterborough (CA)

( * ) Notice: Subject to any disclaimer, the term of this patent is extended or adjusted under 35 U.S.C. 154(b) by 42 days.

(21) Appl. No.: 12/864,065

(22) PCT Filed: Jan. 22, 2009

(86) PCT No.: PCT/CA2009/000102
§ 371 (c)(1),
(2), (4) Date: Jul. 22, 2010

(87) PCT Pub. No.: WO2009/092171
PCT Pub. Date: Jul. 30, 2009

(65) Prior Publication Data
US 2010/0311071 A1 Dec. 9, 2010

Related U.S. Application Data

(60) Provisional application No. 61/011,581, filed on Jan. 22, 2008, provisional application No. 61/133,242, filed on Jun. 27, 2008.

(51) Int. Cl.
*C12Q 1/68* (2006.01)
*C07H 21/04* (2006.01)
*G01N 33/68* (2006.01)

(52) U.S. Cl.
CPC ...... *G01N 33/6893* (2013.01); *C12Q 2600/124* (2013.01); *C12Q 1/6883* (2013.01); *C12Q 2600/156* (2013.01); *G01N 2333/90274* (2013.01); *G01N 2800/347* (2013.01); *C12Q 2600/158* (2013.01)
USPC ......... 435/6.1; 435/6.11; 435/6.12; 435/91.1; 435/91.2

(58) Field of Classification Search
None
See application file for complete search history.

(56) References Cited

U.S. PATENT DOCUMENTS

| 2003/0092019 A1* | 5/2003 | Meyer et al. ............ 435/6 |
| 2006/0149048 A1 | 7/2006 | Wisnewski et al. |
| 2009/0123957 A1 | 5/2009 | Wisnewski et al. |

FOREIGN PATENT DOCUMENTS

| WO | 01/11026 | 2/2001 |
| WO | W 01/11026 | * 2/2001 |

OTHER PUBLICATIONS

Sayasith et al. (Genbank Accession No. AY927786, Mar. 1, 2006).*
Tacher et al. (J. of Heredity, vol. 96, No. 7, pp. 812-816, 2005).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Lucentini (The Scientist; 2004, vol. 24, p. 20).*
Simmons, D.L., et al., Cyclooxygenase Isozymers: The Biology of Prostaglandin Synthesis and Inhibition, Pharmacol. Rev., 2004, pp. 387-437, vol. 56.
Peeters, D., et al., Juvenile Nephropathy in a Boxer, a Rottweiler, a Collie and an Irish Wolfhound, Aust. Vet. J., Mar. 2000, pp. 162-165, vol. 78, No. 3.
Breyer, M.D and Harris, R.C., Cyclooxygenase 2 and the Kidney, Curr. Opin. Nephrol. Hypertension, 2001, pp. 89-98, vol. 10.
"Human C-reactive protein (CRP) associated marker DNA SEQ ID No. 1046." Database Geneseq (Online), Jan. 26, 2006.
Bovee, K.C., "Renal Dysplasia in Shih Tzu Dogs", The 28th Congress of the World Small Animal Veterinary Association Proceedings Online, Oct. 24, 2003.
Thatcher, S., "Update* The RD test is now available see www. dogenes.com for details", Nov. 2006 Renal Dysplasia Update (Online), Nov. 5, 2006.
Dinchuk, J.E., et al., "Renal abnormalities and an altered inflammatory response in mice lacking cyclooxygenase II", Nature: International Weekly Journal of Science, Nature Publishing Group, United Kingdom, Nov. 1, 1995, vol. 378, pp. 406-409.
Sellick, G.S., et al., "Genomewide linkage searches for Mendelian disease loci can be efficiently conducted using high-density SNP genotyping arrays", Nucleic Acids Research, Nov. 16, 2004, vol. 32, No. 20, pp. E164-E164.
Rossetti, S., et al., "Genotype-Phenotype correlations in autosomal dominant and autosomal recessive polycystic kidney disease", Journal of the American Society of Nephrology, vol. 18, No. 5, Apr. 11, 2007, pp. 1374-1380.
"*Canis familiaris* cyclooxygenase 2 (COX-2) gene, promoter region and 5' UTR.", Database Embl. (Online), Mar. 2, 2006, Accession No. AY927786.
Whiteley, M.H., "Juvenile Renal Dysplasia (JRD) DNA Testing", URL:http://www.gsdhelp.info/renal/jrdtesting.htm, May 17, 2008.
Whiteley, M.H., et al., "Novel allelic variants in the canine cyclooxygenase-2 (Cox-2) promoter are associated with renal dysplasia in dogs", Plos One, vol. 6, No. 2, Jan. 1, 2011, pp. E16684-E16684.

* cited by examiner

*Primary Examiner* — Jeanine A Goldberg
(74) *Attorney, Agent, or Firm* — Bereskin & Parr LLP; Melanie Szweras

(57) ABSTRACT

The application relates to Canine Cox2 allelic variants associated with Juvenile Renal Dysplasia, primer and probe compositions and methods and kits useful in detecting, monitoring and diagnosing Juvenile Renal Dysplasia or calcium oxalate stones.

5 Claims, 7 Drawing Sheets

Figure 1 ttgtcaaacaacttgcagcgagcgtctggagcacgctcgggaactccgc<u>a</u>
<u>cagcgcctgcctcctcc</u>agcgccgcagccccgagcccaggacgggaacgc
ctccgccgccgcctccgcctccgccgccgcctctgccaccgcccgcgctc
cgcccgcgccccgcccgccgccgcgATGCTGGCCCGCGCCCTGGTGCTCT
GCGCCGCCCTGGCGGT<u>CGTCCGCGCAG</u><u>gtgggtacct</u>ggctccccgccgc
Ggggactcctcggctgggtgat (SEQ ID NO:5)

Figure 2A

```
  1 ACAGCGCCTGCCTCCTCCAGCGCCGCAGCCCCGAGCCCAGGACGGGAACGCCTCCGCCGC
    ||||||||||||||||||||||||||||||||||||||||||||||||||||||||||
  1 ACAGCGCCTGCCTCCTCCAGCGCCGCAGCCCCGAGCCCAGGACGGGAACGCCTCCGCC--

61 CGCCTCCGCCTCCGCCGCCGCCTCTGCCACCGCCCGCGCTCCGCCCGCGCCCCGCCCGCC
           ||||||||||||||||||||| ||||              ||||||||||||||||||||
 55 ----TCCGCCTCCGCCGCCGCCTCCGCCA-----------CCGCCCGCGCCCCGCCCGCC

121 GCCGCGATGCTGGCCCGCGCCCTGGTGCTCTGCGCCGCCCTGGCGGTCGTCCGCGCAGGT
         ||||||||||||||||||||||||||||||||||||||||||||||||||||||||
104 GCCGCGATGCTGGCCCGCGCCCTGGTGCTCTGCGCCGCCCTGGCGGTCGTCCGCGCAGGT

181 GGGTACCT (WT)
    ||||||||
164 GGGTACCT (allelic variant 1)

1 ACAGCGCCTGCCTCCTCCAGCGCCGCAGCCCCGAGCCCAGGACGGGAACGCCTCCGCCGC
    ||||||||||||||||||||||||||||||||||||||||||||||||||||
  1 ACAGCGCCTGCCTCCTCCAGCGCCGCAGCCCCGAGCCCAGGACGGGAACGCCT------C

61 CGCCTCCGCCTCCGCCGCCGCCTCTGCCACCGCCCGCGCTCCGCCCGCGCCCCGCCCGCC
           ||||||||||||||||||||| ||||              ||||||||||||||||||||
 55 CGCCTCCGCCTCCGCCGCCGCCTCCGCCA-----------CCGCCCGCGCCCCGCCCGCC

121 GCCGCGATGCTGGCCCGCGCCCTGGTGCTCTGCGCCGCCCTGGCGGTCGTCCGCGCAGGT
         ||||||||||||||||||||||||||||||||||||||||||||||||||||||||
104 GCCGCGATGCTGGCCCGCGCCCTGGTGCTCTGCGCCGCCCTGGCGGTCGTCCGCGCAGGT

181 GGGTACCT (WT)
    ||||||||
164 GGGTACCT (allelic variant 1)

Consensus allele 1: (SEQ ID NO:1)
ACAGCGCCTG CCTCCTCCAG CGCCGCAGCC CCGAGCCCAG GACGGGAACG CCTCCGCCTC  60
CGCCTCCGCC GCCGCCTCCG CCACCGCCCG CGCCCCGCCC GCCGCCGCGA TGCTGGCCCG 120
CGCCCTGGTG CTCTGCGCCG CCCTGGCGGT CGTCCGCGCA GGTGGGTACC T          171
```

Figure 2B

```
  1 ACAGCGCCTGCCTCCTCCAGCGCCGCAGCCCCGAGCCCAGGACGGGAA------------
    ||||||||||||||||||||||||||||||||||||||||||||||||
  1 ACAGCGCCTGCCTCCTCCAGCGCCGCAGCCCCGAGCCCAGGACGGGAACGCCTCCGCCTC

49 CGCCTCCGCCGCCGCCTCCGCCTCCGCCGCCGCCTCTGCCACCGCCCGCGCTCCGCCCGC
    ||||||||||||||||||||||||||||||||||||||||||||||||||||||||||||
 61 CGCCTCCGCCGCCGCCTCCGCCTCCGCCGCCGCCTCTGCCACCGCCCGCGCTCCGCCCGC

109 GCCCGCCCGCCGCCGCGATGCTGGCCCGCGCCCTGGTGCTCTGCGCCGCCCTGGCGGTC
    ||||||||||||||||||||||||||||||||||||||||||||||||||||||||||||
121 GCCCGCCCGCCGCCGCGATGCTGGCCCGCGCCCTGGTGCTCTGCGCCGCCCTGGCGGTC

169 GTCCGCGCAGGTGGGTACCT (WT)
    ||||||||||||||||||||
181 GTCCGCGCAGGTGGGTACCT (allelic variant 2, SEQ ID NO:2)
```

Figure 2C

```
  1 ACAGCGCCTGCCTCCTCCAGCGCCGCAGCCCCGAGCCCAGGACGGGAA------------
    ||||||||||||||||||||||||||||||||||||||||||||||||
  1 ACAGCGCCTGCCTCCTCCAGCGCCGCAGCCCCGAGCCCAGGACGGGAACGCCTCCGCCTC

48 ------------CGCCTCCGCCGCCGCCTCCGCCTCCGCCGCCGCCTCTGCCACCGCCCG
                ||||||||||||||||||||||||||||||||||||||||||||||||
 61 CGCCTCCGCCGCCGCCTCCGCCGCCGCCTCCGCCTCCGCCGCCGCCTCTGCCACCGCCCG

97 CGCTCCGCCCGCGCCCCGCCCGCCGCCGCGATGCTGGCCCGCGCCCTGGTGCTCTGCGCC
    ||||||||||||||||||||||||||||||||||||||||||||||||||||||||||||
121 CGCTCCGCCCGCGCCCCGCCCGCCGCCGCGATGCTGGCCCGCGCCCTGGTGCTCTGCGCC

157 GCCCTGGCGGTCGTCCGCGCAGGTGGGTACCT (WT)
    ||||||||||||||||||||||||||||||||
181 GCCCTGGCGGTCGTCCGCGCAGGTGGGTACCT (allelic variant 3, SEQ ID
NO:3)
```

Figure 2D

```
  1 ACAGCGCCTGCCTCCTCCAGCGCCGCAGCCCCGAGCCCAGGACGGGAACGCCTCCGCCGC
    ||||||||||||||||||||||||||||||||||||||||||||||||||||||||||
  1 ACAGCGCCTGCCTCCTCCAGCGCCGCAGCCCCGAGCCCAGGACGGGAACGCCTCCGCC--

61 CGCCTCCGCCTCCGCCGCCGCCTCTGCCACCGCCCGCGCTCCGCCCGCGCCCCGCCCGCC
            ||||||||||||||||||| |||||||||||||||||||||||||||||||||||
 55 ----TCCGCCTCCGCCGCCGCCTCCGCCACCGCCCGCGCTCCGCCCGCGCCCCGCCCGCC

121 GCCGCGATGCTGGCCCGCGCCCTGGTGCTCTGCGCCGCCCTGGCGGTCGTCCGCGCAGGT
    ||||||||||||||||||||||||||||||||||||||||||||||||||||||||||
115 GCCGCGATGCTGGCCCGCGCCCTGGTGCTCTGCGCCGCCCTGGCGGTCGTCCGCGCAGGT

181 GGGTACCT (WT)
    ||||||||
175 GGGTACCT (allelic variant 4)

1 ACAGCGCCTGCCTCCTCCAGCGCCGCAGCCCCGAGCCCAGGACGGGAACGCCTCCGCCGC
    |||||||||||||||||||||||||||||||||||||||||||||||||||||    |
  1 ACAGCGCCTGCCTCCTCCAGCGCCGCAGCCCCGAGCCCAGGACGGGAACGCCT------C

61 CGCCTCCGCCTCCGCCGCCGCCTCTGCCACCGCCCGCGCTCCGCCCGCGCCCCGCCCGCC
    |||||||||||||||||||||||| |||||||||||||||||||||||||||||||||||
 55 CGCCTCCGCCTCCGCCGCCGCCTCCGCCACCGCCCGCGCTCCGCCCGCGCCCCGCCCGCC

121 GCCGCGATGCTGGCCCGCGCCCTGGTGCTCTGCGCCGCCCTGGCGGTCGTCCGCGCAGGT
    ||||||||||||||||||||||||||||||||||||||||||||||||||||||||||
115 GCCGCGATGCTGGCCCGCGCCCTGGTGCTCTGCGCCGCCCTGGCGGTCGTCCGCGCAGGT

181 GGGTACCT (WT)
    ||||||||
175 GGGTACCT (allelic variant 4)
```

Allele 4 Consensus:
ACAGCGCCTG CCTCCTCCAG CGCCGCAGCC CCGAGCCCAG GACGGGAACG CCTCCGCCTC 60
CGCCTCCGCC GCCGCCTCCG CCACCGCCCG CGCTCCGCCC GCGCCCCGCC CGCCGCCGCG 120
ATGCTGGCCC GCGCCCTGGT GCTCTGCGCC GCCCTGGCGG TCGTCCGCGC AGGTGGGTAC 180
CT (SEQ ID NO:4)

Figure 3

Part of Intron1/Exon2/intron2/Exon3/part of intron3 ttatttatgtaaagttgatccatacaattcaatgttaaatgaagattaaa
gaatgaatcatttactgtccttactttttttgtagCAAATCCTTGCTGT
TCCCACCCATGTCAAAACCAAGGTATTTGTATGAGCACAGGATTTGACCA
GTATAAGTGTGACTGTACCCGAACAGGATTCTACGGCGAAAACTGCTCAA
CACgtaagtgtgcccttgggggtgccctcatttggactggggatatgtcc
agttaccaatttRcatactagtgtctcataatgggtcctattaatctttc
cctcttctgttttttgcagCGGAATTTCTGACAAGAATAAAATTATACCTG
AAACCCACTCCAAATACAGTACACTACATACTTACCCACTTCAAGGGAGT
CTGGAACATTGTCAATAACATCCCCTTCCTGCGAAATACAATTATGAAAT
ATGTGTTGACATgtaagtacaagtctctttctaaggttttcaatttcctc
aaagaaaaatgttctttataagactttagatt (SEQ ID NO:6)

SNP =R( A IN MINIATURE SCHNAUZER)
       (G IN POODLE)

EXON 4 AND FLANKS gtgccactttgcacgttgtacaataaaagtgaacattgatatgtcttgcg
tataggaacaaataaaacaatattttttttcttaaatttcagCCCGGTCA
CATTTGATTGAGAGTCCACCAACTTATAATGTGAACTACGGCTATAAAAG
CTGGGAAGCCTTTTCTAACCTCTCCTATTATACCAGAGCTCTTCCCCCTG
TACCTGATGACTGTCCAACACCCATGGGTGTGAAAGgtgagtacggggag
gcagttagacatgtattcattgcaatagggattgggttgctacctagaaa
attcagccctgaactatcatttatttgttaataaaagcatattttttgct
tgaggatatctgtgaatctca (SEQ ID NO:7)

EXON 5 AND FLANKS tttctcctgtaagtgaagaaagccccagactaaattgacattcactgctt
gcttgaacttgtaaatgaattcttatcttagctttctcattcttcagGCA
AGAAAGAGCTTCCTGATTCAAAAGAGATTGTGGAAAAGTTTCTTCTGCGA
AGAAAGTTCATTCCTGATCCCCAAGGCACCAATATGATGTTTGCATTCTT
TGCCCAGCACTTTACCCATCAATTTTTCAAGACAGATCATAAGCGAGGAC
CAGCTTTCACCAAAGGATTGGGCCATGGGgtaagaaattcaaattatagc
Aaaagtca (SEQ ID NO:8)

EXON 6 AND 7 FLANKS atgatgaattacattatagaaactttatagaacttcaacagcaacaaatt
aaaattttccataatcttccagGTGGACTTAAATCATGTTTATGGGGAA

Figure 3 (Continued)

ACTTTGGATAGACAACATAAACTGCGCCTTTTCAAGGATGGAAAAATGAA
ATATCAGgtttgttccattggaatattaagaattgactcacaactaaccc
atatttaaaaacttcccctgattaaaatttaatgtttgtactactgttgt
ttcttagGTAATTGATGGAGAGGTGTATCCTCCTACCGTCAAAGATACTC
AGGTCGAGATGATCTACCCACCTCATGTTCCTGAACACCTGCAGTTTGCT
GTGGGCCAGGAGGTCTTTGGTCTGGTGCCTGGTCTGATGATGTATGCCAC
CATTTGGCTGCGGGAGCATAACAGAGTGTGTGATGTGCTTAAACAGGAGC
ACCCAGAATGGGATGATGAGCGGTTATTCCAGACGAGCAGGCTAATACTg
ATAGgtaagcaagaagagaaaataa (SEQ ID NO:9)

EXON 8 AND FLANKS atttttttgttgttgttgtgtaaatagGAGAAACCATTAAGATTGTGATT
GAAGACTATGTACAACACTTGAGTGGCTATCACTTCAAGCTGAAGTTTGA
CCCAGAGCTGCTTTTCAACCAACAATTCCAGTACCAAAACCGCATTGCTG
CTGAGTTTAACACACTCTACCACTGGCATCCCCTCCTGCCTGACACCTTG
CAAATAGATGACCAGGAGTACAATTTCCAACAGTTTATCTACAACAACTC
TATATTATTGGAACATGGCCTTACCCAGTTTGTGGAATCATTCAGCAGGC
AAATTGCTGGCAGGtaagccttgttattgaaaaaacaaaggactaatca
Gaatttctgccaccaaagtgatctttc (SEQ ID NO:10)

EXON 9 AND FLANKS aaagtagagatcatcataaagatgcctaagaccttattctacaatttaat
tcatttcccatagGTTGCCGGTGGCAGGAATGTTCCAGCTGCAGTACAAC
AAGTAGCAAAAGCTTCGATTGACCAGAGCAGACAGATGAAATACCAGTCT
CTTAATGAGTATCGCAAACGCTTAGGCTGAAGCCCTATACATCATTCGA
AGAACTTACAGgtgagagaaacttcttaagaatcaagggtcaaatggaaa
Caagttgaaagggaattgagcaaagggtta (SEQ ID NO:11)

EXON 10 AND FLANKS
gagcaaagggttaaaactttttttttttggtaaagttttttatacattagt
tgaatatctgtttttgtcaccttcacagGAGAGAAGGAAATGGCTGCGGG
GTTGGAGGCCCTTTATGGTGATATTGATGCCATGGAGCTGTATCCTGCCC
TCTTGGTAGAAAAGCCTCGTCCAGATGCCATCTTTGGTGAGACCATGGTA
GAAATGGGAGCACCATTCTCCTTGAAAGGACTTATGGGTAATCCCATCTG
TTCACCTGACTACTGGAAGCCTAGCACCTTTGGTGGAGAAGTAGGCTTTA
AAATCATCAACACTGCCTCAATCCAGTCTCTCATCTGCAATAACGTGAAG
GGCTGTCCATTCACTGCATTCTCTGTTCAAGACGGACAACTCACCAAAAC
AGTCACCATTAATGCAAGCTCTTCGCACTCCGGTCTAGATGACATCAATC
CCACAGTCCTACTGAAAGAACGGTCAACTGAACTATAGaagcctg (SEQ ID NO:12)

1 2 3 4 5 6

SEQUENCE LISTING

<160> NUMBER OF SEQ ID NOS: 32

<210> SEQ ID NO 1
<211> LENGTH: 171
<212> TYPE: DNA
<213> ORGANISM: Canis lupus familiaris

<400> SEQUENCE: 1

```
acagcgcctg cctcctccag cgccgcagcc ccgagcccag gacgggaacg cctccgcctc      60
cgcctccgcc gccgcctccg ccaccgcccg cgccccgccc gccgccgcga tgctggcccg     120
cgccctggtg ctctgcgccg ccctggcggt cgtccgcgca ggtgggtacc t              171
```

<210> SEQ ID NO 2
<211> LENGTH: 200
<212> TYPE: DNA
<213> ORGANISM: Canis lupus familiaris

<400> SEQUENCE: 2

```
acagcgcctg cctcctccag cgccgcagcc ccgagcccag gacgggaacg cctccgcctc      60
cgcctccgcc gccgcctccg cctccgccgc cgcctctgcc accgccgcg ctccgcccgc     120
gccccgcccg ccgccgcgat gctggcccgc gccctggtgc tctgcgccgc cctggcggtc     180
gtccgcgcag gtgggtacct                                                 200
```

<210> SEQ ID NO 3
<211> LENGTH: 212
<212> TYPE: DNA
<213> ORGANISM: Canis lupus familiaris

<400> SEQUENCE: 3

```
acagcgcctg cctcctccag cgccgcagcc ccgagcccag gacgggaacg cctccgcctc      60
cgcctccgcc gccgcctccg ccgccgcctc cgcctccgcc gccgcctctg ccaccgcccg     120
cgctccgccc gcgccccgcc cgccgccgcg atgctggccc gcgccctggt gctctgcgcc     180
gccctggcgg tcgtccgcgc aggtgggtac ct                                   212
```

```
<210> SEQ ID NO 4
<211> LENGTH: 182
<212> TYPE: DNA
<213> ORGANISM: Canis lupus familiaris

<400> SEQUENCE: 4
acagcgcctg cctcctccag cgccgcagcc ccgagcccag gacgggaacg cctccgcctc      60
cgcctccgcc gccgcctccg ccaccgcccg cgctccgccc gcgccccgcc cgccgccgcg     120
atgctggccc gcgccctggt gctctgcgcc gccctggcgg tcgtccgcgc aggtgggtac     180
ct                                                                    182

<210> SEQ ID NO 5
<211> LENGTH: 272
<212> TYPE: DNA
<213> ORGANISM: Canis lupus familiaris

<400> SEQUENCE: 5
ttgtcaaaca acttgcagcg agcgtctgga gcacgctcgg gaactccgca cagcgcctgc      60
ctcctccagc gccgcagccc cgagcccagg acgggaacgc ctccgccgcc gcctccgcct     120
ccgccgccgc ctctgccacc gcccgcgctc gcccgcgcc cgccgccgcg ccgcgatgct     180
ggcccgcgcc ctggtgctct gcgccgccct ggcggtcgtc cgcgcaggtg ggtacctggc     240
tccccgccgc ggggactcct cggctgggtg at                                   272

<210> SEQ ID NO 6
<211> LENGTH: 532
<212> TYPE: DNA
<213> ORGANISM: Canis lupus familiaris
<220> FEATURE:
<221> NAME/KEY: misc_feature
<222> LOCATION: (263)..(263)
<223> OTHER INFORMATION: SNP=R (A in miniature Schnauzer)
      (G in Poodle)

<400> SEQUENCE: 6
ttatttatgt aaagttgatc catacaattc aatgttaaat gaagattaaa gaatgaatca      60
tttactgtcc ttactttttt ttgtagcaaa tccttgctgt tcccacccat gtcaaaacca     120
aggtatttgt atgagcacag gatttgacca gtataagtgt gactgtaccc gaacaggatt     180
ctacggcgaa aactgctcaa cacgtaagtg tgcccttggg ggtgccctca tttggactgg     240
ggatatgtcc agttaccaat ttrcatacta gtgtctcata tgggtccta ttaatctttc     300 cctcttctgt ttttgcagcg gaatttctga caagaataaa attatacctg aaacccactc     360
caaatacagt acactacata cttacccact tcaagggagt ctggaacatt gtcaataaca     420
tccccttcct gcgaaataca attatgaaat atgtgttgac atgtaagtac aagtctcttt     480
ctaaggtttt caatttcctc aaagaaaaat gttctttata agactttaga tt              532

<210> SEQ ID NO 7
<211> LENGTH: 371
<212> TYPE: DNA
<213> ORGANISM: Canis lupus familiaris

<400> SEQUENCE: 7
gtgccacttt gcacgttgta caataaaagt gaacattgat atgtcttgcg tataggaaca      60
aataaaacaa tattttttt cttaaatttc agcccggtca catttgattg agagtccacc     120
aacttataat gtgaactacg gctataaaag ctgggaagcc ttttctaacc tctcctatta     180
taccagagct cttccccctg tacctgatga ctgtccaaca cccatgggtg tgaaaggtga     240
```

```
gtacggggag gcagttagac atgtattcat tgcaataggg attgggttgc tacctagaaa      300
attcagccct gaactatcat ttatttgtta ataaaagcat attttttgct tgaggatatc      360
tgtgaatctc a                                                           371

<210> SEQ ID NO 8
<211> LENGTH: 308
<212> TYPE: DNA
<213> ORGANISM: Canis lupus familiaris

<400> SEQUENCE: 8
tttctcctgt aagtgaagaa agccccagac taaattgaca ttcactgctt gcttgaactt       60
gtaaatgaat tcttatctta gctttctcat tcttcaggca agaaagagct tcctgattca      120
aaagagattg tggaaaagtt tcttctgcga agaaagttca ttcctgatcc ccaaggcacc      180
aatatgatgt ttgcattctt tgcccagcac tttacccatc aattttttcaa gacagatcat    240 aagcgaggac cagctttcac caaggattgg ggccatgggg taagaaattc aaattatagc      300
aaaagtca                                                               308

<210> SEQ ID NO 9
<211> LENGTH: 525
<212> TYPE: DNA
<213> ORGANISM: Canis lupus familiaris

<400> SEQUENCE: 9
atgatgaatt acattataga aactttatag aacttcaaca gcaacaaatt aaaattttc        60 cataatcttc caggtggact taaatcatgt ttatggggaa actttggata gacaacataa      120
actgcgcctt ttcaaggatg gaaaaatgaa atatcaggtt tgttccattg gaatattaag      180
aattgactca caactaaccc atatttaaaa acttcccctg attaaaattt aatgtttgta      240
ctactgttgt ttcttaggta attgatggag aggtgtatcc tcctaccgtc aaagatactc      300
aggtcgagat gatctaccca cctcatgttc ctgaacacct gcagtttgct gtgggccagg      360
aggtctttgg tctggtgcct ggtctgatga tgtatgccac catttggctg cgggagcata      420
acagagtgtg tgatgtgctt aaacaggagc acccagaatg ggatgatgag cggttattcc      480
agacgagcag gctaatactg ataggtaagc aagaagagaa aataa                      525

<210> SEQ ID NO 10
<211> LENGTH: 377
<212> TYPE: DNA
<213> ORGANISM: Canis lupus familiaris

<400> SEQUENCE: 10
atttttttgt tgttgttgtg taaataggag aaaccattaa gattgtgatt gaagactatg       60
tacaacactt gagtggctat cacttcaagc tgaagtttga cccagagctg cttttcaacc      120
aacaattcca gtaccaaaac cgcattgctg ctgagtttaa cacactctac cactggcatc      180
ccctcctgcc tgacaccttg caaatagatg accaggagta caatttccaa cagtttatct      240
acaacaactc tatattattg gaacatggcc ttacccagtt tgtggaatca ttcagcaggc      300
aaattgctgg cagggtaagc cttgttattg aaaaaacaaa ggactaatca gaatttctgc      360
caccaaagtg atctttc                                                     377

<210> SEQ ID NO 11
<211> LENGTH: 280
<212> TYPE: DNA
<213> ORGANISM: Canis lupus familiaris
```

<400> SEQUENCE: 11

```
aaagtagaga tcatcataaa gatgcctaag accttattct acaatttaat tcatttccca      60
taggttgccg gtggcaggaa tgttccagct gcagtacaac aagtagcaaa agcttcgatt     120
gaccagagca gacagatgaa ataccagtct cttaatgagt atcgcaaacg ctttaggctg     180
aagccctata catcattcga agaacttaca ggtgagagaa acttcttaag aatcaagggt     240
caaatggaaa caagttgaaa gggaattgag caaagggtta                           280
```

<210> SEQ ID NO 12
<211> LENGTH: 495
<212> TYPE: DNA
<213> ORGANISM: Canis lupus familiaris

<400> SEQUENCE: 12

```
gagcaaaggg ttaaaacttt ttttttttggt aaagtttttt atacattagt tgaatatctg     60
tttttgtcac cttcacagga gagaaggaaa tggctgcggg gttggaggcc ctttatggtg    120
atattgatgc catggagctg tatcctgccc tcttggtaga aaagcctcgt ccagatgcca    180
tctttggtga gaccatggta gaaatgggag caccattctc cttgaaagga cttatgggta    240
atcccatctg ttcacctgac tactggaagc ctagcaacctt tggtggagaa gtaggctta   300 aaatcatcaa cactgcctca atccagtctc tcatctgcaa taacgtgaag gctgtccat    360 tcactgcatt ctctgttcaa gacggacaac tcaccaaaac agtcaccatt aatgcaagct    420
cttcgcactc cggtctagat gacatcaatc ccacagtcct actgaaagaa cggtcaactg   480
aactatagaa gcctg                                                     495
```

<210> SEQ ID NO 13
<211> LENGTH: 19
<212> TYPE: DNA
<213> ORGANISM: Canis lupus familiaris

<400> SEQUENCE: 13

```
acagcgcctg cctcctcca                                                  19
```

<210> SEQ ID NO 14
<211> LENGTH: 22
<212> TYPE: DNA
<213> ORGANISM: Canis lupus familiaris

<400> SEQUENCE: 14

```
aggtacccac ctgcgcggac ga                                              22
```

<210> SEQ ID NO 15
<211> LENGTH: 24
<212> TYPE: DNA
<213> ORGANISM: Canis lupus familiaris

<400> SEQUENCE: 15

```
ttgtcaaaca acttgcagcg agcg                                            24
```

<210> SEQ ID NO 16
<211> LENGTH: 19
<212> TYPE: DNA
<213> ORGANISM: Canis lupus familiaris

<400> SEQUENCE: 16

```
atcacccagc cgaggagtc                                                  19
```

```
<210> SEQ ID NO 17
<211> LENGTH: 24
<212> TYPE: DNA
<213> ORGANISM: Canis lupus familiaris

<400> SEQUENCE: 17
cctggttgaa cgttgttggc ctta                                          24

<210> SEQ ID NO 18
<211> LENGTH: 22
<212> TYPE: DNA
<213> ORGANISM: Canis lupus familiaris

<400> SEQUENCE: 18
cccactcagg ttcattctct ca                                            22

<210> SEQ ID NO 19
<211> LENGTH: 25
<212> TYPE: DNA
<213> ORGANISM: Canis lupus familiaris

<400> SEQUENCE: 19
ccatggacca ctggtttaca atagg                                         25

<210> SEQ ID NO 20
<211> LENGTH: 24
<212> TYPE: DNA
<213> ORGANISM: Canis lupus familiaris

<400> SEQUENCE: 20
gagattcaca gatatcctca agca                                          24

<210> SEQ ID NO 21
<211> LENGTH: 22
<212> TYPE: DNA
<213> ORGANISM: Canis lupus familiaris

<400> SEQUENCE: 21
ctcctgtaag tgaagaaagc cc                                            22

<210> SEQ ID NO 22
<211> LENGTH: 20
<212> TYPE: DNA
<213> ORGANISM: Canis lupus familiaris

<400> SEQUENCE: 22
atgcgtgtgt gtgcttgagt                                               20

<210> SEQ ID NO 23
<211> LENGTH: 26
<212> TYPE: DNA
<213> ORGANISM: Canis lupus familiaris

<400> SEQUENCE: 23
actatttagt ggttgtgaga gaaacg                                        26

<210> SEQ ID NO 24
<211> LENGTH: 24
<212> TYPE: DNA
<213> ORGANISM: Canis lupus familiaris

<400> SEQUENCE: 24
agtaacatgc cagctttctc tggg                                          24
```

```
<210> SEQ ID NO 25
<211> LENGTH: 24
<212> TYPE: DNA
<213> ORGANISM: Canis lupus familiaris

<400> SEQUENCE: 25
acaagattgc atttcagttg cttg                                          24

<210> SEQ ID NO 26
<211> LENGTH: 24
<212> TYPE: DNA
<213> ORGANISM: Canis lupus familiaris

<400> SEQUENCE: 26
cagaaagatc actttggtgg caga                                          24

<210> SEQ ID NO 27
<211> LENGTH: 26
<212> TYPE: DNA
<213> ORGANISM: Canis lupus familiaris

<400> SEQUENCE: 27
gcattagtct tccctccttt gtaccc                                        26

<210> SEQ ID NO 28
<211> LENGTH: 24
<212> TYPE: DNA
<213> ORGANISM: Canis lupus familiaris

<400> SEQUENCE: 28
accatggtct caccaaagat ggca                                          24

<210> SEQ ID NO 29
<211> LENGTH: 24
<212> TYPE: DNA
<213> ORGANISM: Canis lupus familiaris

<400> SEQUENCE: 29
gttgaaaggg aattgagcaa aggg                                          24

<210> SEQ ID NO 30
<211> LENGTH: 25
<212> TYPE: DNA
<213> ORGANISM: Canis lupus familiaris

<400> SEQUENCE: 30
caggcttcta tagttcagtt gaccg                                         25

<210> SEQ ID NO 31
<211> LENGTH: 12
<212> TYPE: DNA
<213> ORGANISM: Canis lupus familiaris

<400> SEQUENCE: 31
cgcctccgcc tc                                                       12

<210> SEQ ID NO 32
<211> LENGTH: 24
<212> TYPE: DNA
<213> ORGANISM: Canis lupus familiaris

<400> SEQUENCE: 32
cgcctccgcc tccgcctccg ccgc                                          24
```

COMPOSITIONS AND METHODS FOR DETECTING JUVENILE RENAL DYSPLASIA OR CALCIUM OXALATE STONES IN DOGS

CROSS REFERENCE TO RELATED APPLICATIONS

This is a national stage application of PCT/CA2009/000102 filed on Jan. 22, 2009 which claims priority from U.S. provisional applications 61/011,581 filed on Jan. 22, 2008 and 61/133,242 filed Jun. 27, 2008, all of which are incorporated herein by reference in their entirety.

INCORPORATION OF SEQUENCE LISTING

A computer readable form of the Sequence Listing "20247-7_Sequence_Listing.txt" (9,984 bytes), submitted via EFS-WEB and amended on Jul. 20, 2010, is herein incorporated by reference.

FIELD

The present application relates to novel allelic variants of the canine cyclooxygenase 2 (Cox2) gene. In particular, the application relates to methods of detecting and diagnosing Juvenile Renal Dysplasia (JRD) or calcium oxalate stones in dogs through detection of the novel allelic variants or detection of altered expression of canine Cox2.

BACKGROUND

Juvenile Renal Dysplasia (JRD) is an important category of kidney disease in canines and is also sometimes referred to as juvenile nephropathy (Peeters D, Clercx C, Michiels L, Desmecht D, Snaps F, Henroteaux M, Day M J. 2000, Aust. Vet J. 78(3):162-165). Dysplasia is defined as abnormal growth or development of cells or organs. In the case of JRD, the kidney fails to develop properly during embryogenesis in the womb. At birth immature structures consisting of undifferentiated fetal cells or tissue types are found in the kidney. JRD in affected breeds share a common phenotype, characterized by immature glomeruli, and/or tubules and persistent mesenchyme, and defects in the renal cortex.

Many breeds of dogs are affected with JRD, and this has been documented in both veterinary textbooks (Kruger, J. M., Osborne, C. A., et al.: Congenital and Hereditary Disorders of the Kidney; Veterinary Pediatrics Dogs & Cats from Birth to Six Months, $2^{nd}$ edition. (J. D. Hoskins, ed.) W.B.Saunders, Philadelphia, Pa., 1995: pp 401-406), as well as case reports and articles in the scientific literature (Abraham L A, Beck C, Slocombe R F Aust (2003) Vet J. 81(6):336-9; Peeters D, Clercx C, Michiels L, Desmecht D, Snaps F, Henroteaux M, Day M J. (2000). Aust Vet J. 78(3):162-165; Hoppe A, Karlstam E. (2000) J Small Anim Pract., 41(9):422-6; Olenick C L. (1999) Can Vet J.; 40(6):425-6; Schulze C, Meyer H P, Blok A L, Schipper K, van den Ingh T S. (1998) Vet Q. 20(4):146-8; Roels S, Schoofs S, Ducatelle R. (1997) Small Anim Pract. 38(3):115-8; Lobetti R G, Pearson J, Jimenez M. J Small Anim Pract., 37(11):552-5; Kerlin R L, Van Winkle T (1995) J. Vet Pathol. 32(3):327-9; Vilafranca M, Ferrer L. (1994) Vet Pathol. (3):375-7; Morton L D, Sanecki R K, Gordon D E, Sopiarz R L, Bell J S, Sakas P S. (1990) Vet Pathol. (6):455-8; Booth K. (1990) Vet Rec. 127(24):596-7; Nash A S, Creswick J A. (1988) Vet Rec. 123(25):654-5; Robinson W F, Huxtable C R, Gooding J R (1985) Aust Vet J. 62(4):109-12; Manderino D M, DeVries J G, Tamarkin J. (1984) Mod Vet Pract. 65(8):633-5; DiBartola S P, Chew D J, Boyce J T. (1983) J Am Vet Med. Assoc. 183(6):693-6; O'Brien T D, Osborne C A, Yano B L, Barnes D M. (1982) J Am Vet Med. Assoc. 180(6):658-64.)

Breeds most notably affected with JRD include Shih tzus, Lhasa apsos, and Soft Coated Wheaten Terriers and Miniature schnauzers. Other breeds reported in the scientific literature cited above include Golden retriever, Tibetan spaniel, Flat coated retriever, King Charles Cavalier spaniel, Standard Poodle, Cairn terrier, Tibetan terrier, Bull Mastiff, Boxers, Finnish Harriers, Rhodesian ridgeback, Flat coated retriever, Norwegian Elkhound, Bedlington Terriers, Chow Chows, Shetland sheepdogs Rottweilers, Alaskan Malamutes, Yorkshire terriers, Airedale Terriers, Irish Wolfhounds, Keeshonds, Old English sheepdogs, and Collies. There are probably others not yet reported in the veterinary literature as this disease has such a varied phenotype that it is most likely to be reported in breeds with a high frequency of these mutations.

The mode of inheritance of JRD has been widely debated, as this disease can present itself with a wide range of symptoms and pathological findings. Definitive diagnosis of JRD is done by a wedge biopsy that reveals dysplastic lesions, including abnormal ducts, and glomeruli. Individuals with an abnormal biopsy can be asymptomatic, showing no signs of the disease. On the other hand, affected animals may present with classic signs of chronic end stage renal failure or somewhere between these two extremes (see Bovee, 2003 The $28^{th}$ Congress of the World Small Animal Veterinary Association Proceedings). Comprehensive data from biopsies from Shih Tzus presented by Bovee indicate that the mode of inheritance are most consistent with an autosomal dominance pattern with incomplete penetrance. This was largely supported by an outcross of a biopsy positive Shih Tzu with a normal poodle. The resultant progeny showed the presence of fetal glomeruli on biopsy.

The morphological features of JRD in dogs differ slightly from those in man (Picut C A, Lewis R M (1987) Vet Pathol. 24(2):156-63), and therefore selection of genes that are responsible for this disease is somewhat difficult from human disease, however, one possible gene described in mouse that causes renal dyplasia is the Cox2 gene (Ptgs2: Prostaglandin-endoperoxide synthase 2). While this gene is generally associated with biologic events such as injury, inflammation, and proliferation (Hla, T. and Neilson, K. (1993) Proc. Nat. Acad. Sci. 89: 7384-7388; Tazawa, R., Xu, X.-M., Wu, K. K., Wang, L.-H. (1994) Biochem. Biophys. Res. Commun. 203: 190-1999), the knockout mouse model shows abnormal kidney development, including but not limited to an abnormal renal cortex with small immature glomeruli, deteriorating tubules and glomerulosclerosis. Cox2 knockout mice also show increased blood urea nitrogen and circulation creatinine levels, consistent with impaired renal function. All homozygous adult mice showing renal disease are also subject to development of secondary pyelonephritis. The kidneys are generally small and pale in color. (Yu Y, Fan J, Chen X S, Wang D, Klein-Szanto A J, Campbell R L, FitzGerald G A, Funk C D. (2006) Nat. Med. June; 12(6):699-704; Dinchuk J E, Car B D, Focht R J, Johnston J J, Jaffee B D, Covington M B, Contel N R, Eng V M, Collins R J, Czerniak P M, et al. (1995) 1: Nature 378(6555):406-409). Other notable clinical abnormalities in knockout Cox2 mice include, decreased litter size, reduced fertility in females, and patent ductus arteriosis.

SUMMARY

The present inventor has shown that there are small deletions and insertions of DNA sequence just upstream of the ATG start of translation in the canine Cox2 gene that are not present in breeds not known to have JRD or reference canine genomic sequences. In addition, the present inventor has identified single nucleotide polymorphisms upstream of the ATG start of translation. In particular, the present inventor has identified 4 allelic variants of the canine Cox2 gene associated with JRD. The present inventor has also shown that the Cox2 allelic variants are also associated with calcium oxalate stone formation in dogs.

Accordingly, one aspect of the disclosure is a nucleic acid sequence comprising SEQ ID NO:1 or allelic variant 1. Another aspect is a nucleic acid sequence comprising SEQ ID NO:2 or allelic variant 2. A further aspect is a nucleic acid sequence comprising SEQ ID NO:3 or allelic variant 3. Yet another aspect is a nucleic acid sequence comprising SEQ ID NO:4 or allelic variant 4. Also disclosed are probes and primers useful in detecting the allelic variants.

A further aspect of the disclosure is a method to diagnose, detect and monitor whether a dog is at risk of developing Juvenile Renal Dysplasia (JRD) or calcium oxalate stones or whether a dog has JRD or calcium oxalate stones comprising detecting the presence of a Cox2 allelic variant in the dog, wherein the presence of the Cox2 allelic variant is indicative of the dog being at risk of developing JRD or calcium oxalate stones or is indicative of the dog having JRD or calcium oxalate stones.

In yet another aspect, there is provided a method to diagnose, detect and monitor whether a dog is at risk of developing JRD or calcium oxalate stones or whether a dog has JRD or calcium oxalate stones comprising determining the level of expression of Cox2 in a sample, wherein a change in Cox2 expression compared to a control is indicative of the dog being at risk of developing JRD or calcium oxalate stones or is indicative of the dog having JRD or calcium oxalate stones.

In one embodiment, the methods are to diagnose, detect and monitor whether a dog is at risk of developing JRD or whether a dog has JRD. In another embodiment, the methods are to diagnose, detect and monitor whether a dog is at risk of developing calcium oxalate stones or whether a dog has calcium oxalate stones.

The disclosure also provides compositions and kits comprising the nucleic acids described herein and methods of breeding dogs with a reduced risk of JRD or calcium oxalate stones.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 1 shows the sequence to 5' UTR, EXON1, and intron 1—from a poodle, wild type sample of the canine Cox2 that resides on chromosome 7 of the public domain assembled canine genome (SEQ ID NO:5). Diagnostic primers surrounding the mutant alleles are underlined. Exon 1 sequences are shown in upper case, while non-coding sequences are in lower case.

FIG. 2 shows the insertions, deletions and SNPs found within SEQ ID NO:5 corresponding to mutant alleles responsible for JRD or calcium oxalate stones in many canine breeds. Exon 1 of the canine Cox2 gene is shaded. FIG. 2A compares a portion of SEQ ID NO:5 with allelic variation 1 (SEQ ID NO:1). This variation, which represents a deletion of wild type DNA sequences has been found in Miniature schnauzers, Soft Coated wheaten terriers, Shih tzu, Gordon Setter, Lhasa apsos, Boxers, German Shepherd dogs, Golden retrievers, Cairn terriers, Yorkshire terriers, English Cocker spaniels, Shetland sheepdogs and Havanese. FIG. 2B compares a portion of SEQ ID NO:5 with allelic variation 2 (SEQ ID NO:2). This variation, which represents an insertion of DNA sequences, has been found in Soft Coated wheaten terriers, Shih tzu, Gordon Setter, Collies, Lhasa apsos, Tibetan terriers, Shetland sheepdogs, Havanese, Weimaraners, Bernese Mountain Dogs, Poodles, Yorkshire terriers, and Tibetan terriers. FIG. 2C compares a portion of SEQ ID NO:5 with allelic variation 3 (SEQ ID NO:3). This variation, which represents an insertion of DNA sequences, has been found in Miniature schnauzers, Soft Coated wheaten terriers, Shih tzu, Gordon Setter, Tibetan terriers, Lhasa apsos, Boxers, Cairn terriers, Yorkshire terriers, English Cocker spaniels, Portugese water dogs, Bernese Mountain Dogs, Labrador retrievers and Havanese. This variant overlaps allelic variation 2. Allelic variation 2 is boxed. FIG. 2D compares a portion of SEQ ID NO:5 with allelic variation 4 (SEQ ID NO:4). This variation which represents a deletion of DNA sequences has been found in one Gordon Setter. No clinical associations have yet been found with this allele. A SNP also found in this allele is shown in bold. Given the low penetrance of these mutations, more Gordon setters need to be tested. Very few clinical samples are available from this breed. This deletion contains a putative SP1 transcription binding site and therefore is predicted to be involved in the regulation of Cox2.

FIG. 3 shows the nucleotide sequences obtained from clinical samples of a Poodle and a Miniature schnauzer of the coding sequences of the canine Cox2 gene. All of the coding sequences are wild type as compared to the public domain assembled canine genome (Available at the UCSC Genome Bioinformatics website: http://genome.ucsc.edu/)). FIG. 3A shows the nucleotide sequences of Part of Intron1/Exon2/intron2/Exon3/part of intron3 of the canine Cox2 gene (SEQ ID NO:6). FIG. 3B provides the nucleotide sequences of Exon 4 and flanking intronic sequences of the canine Cox2 gene (SEQ ID NO:7). FIG. 3C provides the nucleotide sequences of Exon 5 and flanking intronic sequences of the canine Cox2 gene (SEQ ID NO:8). FIG. 3D provides the nucleotide sequences of Exons 6 and 7 and flanking intronic sequences of the canine Cox2 gene (SEQ ID NO:9). FIG. 3E provides the nucleotide sequences of Exon 8 and flanking intronic sequences of the canine Cox2 gene (SEQ ID NO:10). FIG. 3F provides the nucleotide sequences of Exon 8 and flanking intronic sequences of the canine COX2 gene (SEQ ID NO:11). FIG. 3G provides the nucleotide sequences of Exon 10 and flanking intronic sequences of the canine Cox2 gene (SEQ ID NO:12). Coding sequences are given in upper case.

DETAILED DESCRIPTION

Figure 4:
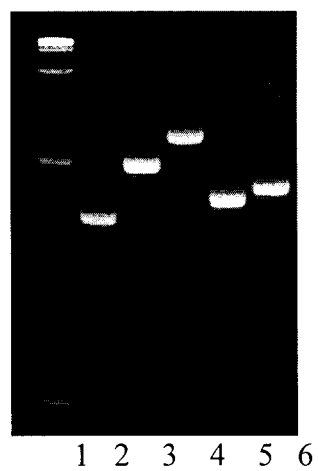
FIG. 4 shows a representation of an electrophoretic separation of PCR amplification of the wild type and mutant alleles found in the 5' UTR of the canine Cox2 gene. The PCR primers used for amplification are underlined in FIG. 1. The first, leftmost, lane contains a 100 bp DNA size ladder. The remaining lanes are as follows: Lane 2 represents allelic variation 1 from FIG. 2A; Lane 3 represents allelic variation 2 from FIG. 2B; Lane 4 represents allelic variation 3 from FIG. 2C; Lane 5 represents allelic variation 4 from FIG. 2D; and Lane 6 represents the wild type allele.

DNA sequencing of the canine Cox2 gene in clinically affected samples from several dog breeds revealed small deletions and insertions of DNA sequence just upstream of the ATG start of translation that were not present in breeds not known to have JRD as well as reference canine genomic sequences. The present application is based on these allelic variants found in many canine breeds to be associated with JRD. These allelic variants showed 100% concordance with the disease in cases. Calcium oxalate bladder stones are also well documented among the breeds that have JRD. The breeds with the highest frequency of the Cox2 mutant alleles, also have the highest incidence of calcium oxalate stones. In particular these include Miniature Schnauzers, Lhasa Apsos, Yorkshire Terriers, Miniature Poodles, and Shih Tzus (the Merck Veterinary Manual (2006)). These breeds have been investigated for the Cox2 alleles, and they all have these variants.

Nucleic Acids

Accordingly, in one aspect of the disclosure, there is provided an isolated nucleic acid sequence comprising a nucleic acid sequence as shown in SEQ ID NO:1 or allelic variant 1. In another embodiment, there is provided an isolated nucleic acid molecule consisting essentially of a nucleic acid sequence as shown in SEQ ID NO:1 or allelic variant 1. Another aspect is an isolated nucleic acid molecule comprising a nucleic acid sequence as shown in SEQ ID NO:2 or allelic variant 2. In an embodiment, there is provided an isolated nucleic acid molecule consisting essentially of a nucleic acid sequence as shown in SEQ ID NO:2 or allelic variant 2. A further aspect is an isolated nucleic acid molecule comprising a nucleic acid sequence as shown in SEQ ID NO:3 or allelic variant 3. In an embodiment, there is provided an isolated nucleic acid molecule consisting essentially of a nucleic acid sequence as shown in SEQ ID NO:3 or allelic variant 3. Yet another aspect is an isolated nucleic acid molecule comprising a nucleic acid sequence as shown in SEQ ID NO:4 or allelic variant 4. In an embodiment, there is provided an isolated nucleic acid molecule consisting essentially of a nucleic acid sequence as shown in SEQ ID NO:4 or allelic variant 4.

"Consisting essentially of a nucleotide sequence" as used herein refers to a nucleotide sequence disclosed, and also encompasses nucleotide sequences which are identical in sequence except for a one base change or substitution therein while retaining the same ability to function to detect JRD or calcium oxalate stone genotype or a mutated JRD or calcium oxalate stone allele.

"Cox2" or "cyclooxygenase-2" as used herein refers to canine Cox2. FIG. 3 shows exemplary sequences of poodle and miniature schnauzer Cox2 nucleotide sequences. It will be appreciated that because the Cox2 gene disclosed herein is substantially homologous to the Cox2 gene throughout the canine species, Cox2 genes and proteins of all dog breeds are contemplated herein.

The term "isolated" refers to a nucleic acid substantially free of cellular material or culture medium when produced by recombinant DNA techniques, or chemical precursors, or other chemicals when chemically synthesized.

"Genetic marker" or "marker" or "allelic variant" as used herein refers to a variable nucleotide sequence (polymorphic) present in the 5'-untranslated region of the canine Cox2 gene. The variable nucleotide sequence may be identified by known techniques in the art, including without limitation, by nucleic acid amplification and observance of a difference in size or sequence of nucleotides due to the polymorphisms. For example, markers can be identified by any one of several techniques know to those skilled in the art, including, without limitation, microsatellite or short tandem repeat (STR) amplification, analyses of restriction fragment length polymorphisms (RFLP), single nucleotide polymorphism (SNP), detection of deletion or insertion sites, and random amplified polymorphic DNA (RAPD) analysis (Cushwa and Medrano, 1996, Animal Biotech. 7:1 1-31).

The term "nucleic acid molecule" is intended to include unmodified DNA or RNA or modified DNA or RNA. For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

One aspect of the present disclosure is thus an isolated nucleic acid molecule comprising a nucleotide sequence selected from the group consisting of:

(a) a nucleic acid sequence as shown in SEQ ID NO:1, 2, 3, or 4, wherein T can also be U;

(b) a nucleic acid sequence that is complementary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c);

(e) a nucleic acid sequence that hybridizes to a nucleic acid sequence of (a), (b), (c) or (d) under stringent hybridization conditions; and (f) a nucleic acid sequence differing from any of the nucleic acid sequences of (a) to (e) in codon sequences due to the degeneracy of the genetic code.

In the sequences referred to above, T can also be U. As previously stated, the disclosure includes isolated DNA molecules having such sequences of nucleotides, and RNA molecules having such sequences. The disclosure thus includes isolated mRNA transcribed from DNA having such a sequence. The disclosure further encompasses nucleic acid molecules that differ from any of the nucleic acid molecules of the disclosure in codon sequences due to the degeneracy of the genetic code.

The disclosure also encompasses nucleic acid sequences or molecules that are analogs of the nucleic acid sequences and molecules described herein. The term "a nucleic acid sequence which is an analog" means a nucleic acid sequence which has been modified as compared to the sequences described herein, such as sequences of (a), (b), or (c), above wherein the modification does not alter the utility of the sequences described herein. The modified sequence or analog may have improved properties over the sequence shown in (a), (b), or (c). One example of a modification to prepare an analog is to replace one of the naturally occurring bases (i.e. adenine, guanine, cytosine or thymidine) of the sequence shown in SEQ ID NO:1, 2, 3, or 4 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID NO:1, 2, 3, or 4. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

In the context of this specification, the term "conserved" describes similarity between sequences. The degree of conservation between two sequences can be determined by optimally aligning the sequences for comparison. Sequences may be aligned using the Omiga software program, Version 1.13. (Oxford Molecular Group, Inc., Campbell, Calif.). The Omiga software uses the Clustal W Alignment algorithms [Higgins et al., 1989; Higgins et al., 1991; Thompson et al. 1994]. Default settings used are as follows: Open gap penalty 10.00; Extend gap penalty 0.05; Delay divergent sequence 40 and Scoring matrix—Gonnet Series. Percent identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

In one aspect, the present disclosure is a nucleic acid molecule that is a conservatively substituted variant of the nucleotide sequence of SEQ ID NO:1, 2, 3, or 4.

Further, it will be appreciated that the disclosure includes nucleic acid molecules comprising nucleic acid sequences having substantial sequence homology with the nucleic acid sequence as shown in SEQ ID NO:1, 2, 3, or 4 or fragments thereof. The term "sequences having substantial sequence homology" means those nucleic acid sequences that have slight or inconsequential sequence variations from these sequences, i.e., the sequences function in substantially the same manner to produce functionally equivalent proteins. The variations may be attributable to local mutations or structural modifications.

Nucleic acid sequences having substantial homology include nucleic acid sequences having at least about 50 percent identity with SEQ ID NO:1, 2, 3, or 4, respectively, or the full-length anti-sense sequence thereto. The level of homology, according to various aspects of the disclosure is at least about 60 percent; at least about 63 percent; at least about 65 percent; at least about 68 percent; at least about 70 percent; at least about 73 percent; at least about 75 percent; at least about 78 percent; at least about 80 percent; at least about 83 percent; at least about 85 percent; at least about 88 percent; at least about 90 percent; at least about 93 percent; at least about 95 percent; or at least about 98 percent. Methods for aligning the sequences to be compared and determining the level of homology between the sequences are described in detail above.

Sequence identity can be calculated according to methods known in the art. Sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "sequence that hybridizes" means a nucleic acid sequence that can hybridize to a sequence of (a), (b), (c) or (d) under stringent hybridization conditions. Appropriate stringency conditions which promote nucleic acid hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10 [Na+])+0.41(% (G+C)−600/I). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt's solution/1.0% SDS at Tm (based on the above equation)−5° C., followed by a wash of 0.2×SSC/0.1% SDS at 60° C. Other appropriate stringency conditions which promote DNA hybridization are, for example, 6×SSC at about 45° C., followed by a wash of 2×SSC at 50° C. The salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 65° C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

Isolated nucleic acid molecules having sequences which differ from the nucleic acid sequence shown in SEQ ID NO:1, 2, 3, or 4 due to degeneracy in the genetic code are also within the scope of the disclosure. Such nucleic acids encode functionally equivalent proteins but differ in sequence from the above-mentioned sequences due to degeneracy in the genetic code.

An isolated nucleic acid molecule of the disclosure which comprises DNA can be isolated by preparing a labelled nucleic acid probe based on all or part of the nucleic acid sequences as shown in SEQ ID NO:1, 2, 3, or 4 and using this labelled nucleic acid probe to screen an appropriate DNA library (e.g. a cDNA or genomic DNA library).

An isolated nucleic acid molecule of the disclosure which is DNA can also be isolated by selectively amplifying a nucleic acid of the disclosure using the polymerase chain reaction (PCR) methods and cDNA or genomic DNA. It is possible to design synthetic oligonucleotide primers from the nucleic acid sequence as shown in SEQ ID NO:1, 2, 3, or 4 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294 5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

A nucleic acid molecule of the disclosure may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

In another aspect, the present disclosure includes a fragment of the nucleotide sequence encoding Cox2, said fragment comprising at least part of the 5'UTR of the Cox2 gene or one of its allelic variants. Such fragments can find usefulness as probes or depending on the fragments may even have biological activity themselves. The complement of the probe can find utility in, for example, manufacture of the probe or inhibition of any activity of the fragment, as the case may be.

The term "probe" refers to a nucleic acid sequence that will hybridize to a nucleic acid target sequence. In one example, the probe hybridizes to SEQ ID NO:1 or SEQ ID NO:2 or SEQ ID NO:3 or SEQ ID NO:4 or their complements. The length of probe depends on the hybridization conditions and the sequences of the probe and nucleic acid target sequence. In one embodiment, the probe is 8-100, 8-200 or 8-500 nucleotides in length, such as 8-10, 11-15, 16-20, 21-25, 26-50, 51-75, 76-100, 101-150 or 151-200 nucleotides in length or at least 200, 250, 400, 500 or more nucleotides in length. In other embodiments, 10, 15, 20 or 25 nucleotides provide a lower end for the aforementioned nucleotide ranges.

Accordingly, in another aspect, the present application provides a composition comprising an isolated nucleic acid sequence that specifically hybridizes to at least one of SEQ ID NO:1, 2, 3, or 4, or their complements. In one embodiment, the composition is useful to detect the presence of the specific Cox2 allelic variants associated with JRD. In another embodiment, the composition is useful to detect the presence of the specific Cox2 allelic variants associated with calcium oxalate stones.

In another aspect, the application provides a composition comprising at least one isolated nucleic acid sequence that specifically hybridizes to SEQ ID NO:1 or its complement, an isolated nucleic acid sequence that specifically hybridizes to SEQ ID NO:2 or its complement, an isolated nucleic acid sequence that specifically hybridizes to SEQ ID NO:3 or its complement, an isolated nucleic acid sequence that specifically hybridizes to SEQ ID NO:4 or its complement. In one embodiment, the composition is useful to detect the presence of the specific Cox2 allelic variants associated with JRD. In another embodiment, the composition is useful to detect the presence of the specific Cox2 allelic variants associated with calcium oxalate stones.

The phrase "specifically hybridizes to SEQ ID NO:1 or its complement" means that under the same conditions, the isolated nucleic acid sequence will not hybridize to the wild type Cox2 sequence shown in SEQ ID NO:5 or its complement. The phrase "specifically hybridizes to SEQ ID NO:2 or its complement" means that under the same conditions, the isolated nucleic acid sequence will not hybridize to the wild type Cox2 sequence shown in SEQ ID NO:5 or its complement. The phrase "specifically hybridizes" to SEQ ID NO:3 means that under the same conditions, the isolated nucleic acid sequence will not hybridize to the wild type Cox2 sequence shown in SEQ ID NO:5 or its complement. The phrase "specifically hybridizes" to SEQ ID NO:4 means that under the same conditions, the isolated nucleic acid sequence will not hybridize to the wild type Cox2 sequence shown in SEQ ID NO:5 or its complement.

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

Allelic variant 1 is shown in SEQ ID NO:1 and FIG. 2A. There are conceptually two alignments of this sequence with the wild type allele. One alignment shows a deletion of 6 nucleotides, GCCGCC at position-68 of the canine Cox2 gene. The other alignment shows a deletion of 6 nucleotides, CCGCCG at position-73 canine Cox2 gene. In both alignments, there is a deletion of 11 nucleotides at position-37. The consensus sequence for this allele is given in FIG. 2A. In addition to these two changes there is a SNP at position-42. This is a "T" in the wild type sequence and a "C" in allele 1. DNA from 12 different dogs with this allelic variant were sequenced and all 12 had the "C" allele.

Allelic variant 2 as shown in SEQ ID NO:2 and FIG. 2B comprises an insertion of 12 nucleotides starting at position-78 of the canine Cox2 gene. In one embodiment, the insertion comprises the nucleotide sequence CGCCTCCGCCTC (SEQ ID NO:31). 7 dogs with allelic variant 2 were sequenced. None of these had the SNP described in allelic variant 1.

Allelic variant 3 as shown in SEQ ID NO:3 comprises an insertion of 24 nucleotides at position-78 of the canine Cox2 gene. In an embodiment, the insertion comprises the nucleotide sequence CGCCTCCGCCTCCGCCTCCGCCGC (SEQ ID NO:32). Four dogs with this allele were DNA sequenced, and none contained the SNP of allelic variant 1.

Allelic variant 4 as shown in SEQ ID NO:4 comprises a deletion of 6 nucleotides as in allelic variant 1. As in allelic variant 1 there are conceptually 2 alignments of this variant with the wild type sequence of the canine Cox2 gene. Both of these are shown in FIG. 2D. One alignment shows a deletion of 6 nucleotides, GCCGCC at position-68. The other alignment shows a deletion of 6 nucleotides, CCGCCG at position-73. This DNA sequence of allelic variant 4 also contains the SNP at position-42 of the wild type sequence. The consensus sequence of allelic variant 4 is shown in FIG. 2D.

Pairs of primers may be selected wherein one primer is upstream of the site of insertion or deletion or SNP of the specific allelic variant of Cox2 and one primer is downstream of the site of insertion or deletion or SNP of the specific allelic variant of Cox2.

Accordingly, in an embodiment, the application provides a composition of two or more isolated nucleic acid sequences that are primers that are able to amplify a region of the 5'UTR of canine Cox2. In one embodiment, one primer is upstream of position-78 and a one primer is downstream of position-37 of the 5'UTR of canine Cox2. In another embodiment, the region of the 5'UTR comprises a nucleotide sequence as shown in SEQ ID NO:1, 2, 3, 4 or 5.

In one embodiment, primers for amplifying the Cox2 allelic variants comprise a forward primer, 5'-ACA GCG CCT GCC TCC TCC A-3' (SEQ ID NO:13); and a reverse primer, 5'-AGG TAC CCA CCT GCG CGG ACG A-3' (SEQ ID NO:14).

It is also within the contemplation of this application that the isolated and purified nucleic acid sequences disclosed herein be incorporated into an appropriate recombinant expression vector, e.g., viral or plasmid, which is capable of transforming an appropriate host cell, either eukaryotic (e.g., mammalian) or prokaryotic (e.g., E. coli). Such DNA may involve alternate nucleic acid forms, such as cDNA, gDNA, and DNA prepared by partial or total chemical synthesis. The DNA may also be accompanied by additional regulatory elements, such as promoters, operators and regulators, which are necessary and/or may enhance the expression of the Cox2 gene product. In this way, cells may be induced to overexpress the Cox2 gene, thereby generating desired amounts of the target Cox2 protein. It is further contemplated that the canine Cox2 polypeptide sequence may be utilized to manufacture canine Cox2 protein using standard synthetic methods.

Diagnostic Methods

The nucleic acid molecules of the disclosure can be used to diagnose, detect and monitor Juvenile Renal Dysplasia (JRD) or calcium oxalate stones. Further, since the allelic variants identified are in the untranslated promoter region, levels of Cox2 expression are likely disturbed. Thus, the presence of an allelic variant or determination of nucleic acid expression levels could assist not only in identifying JRD or calcium oxalate stones or a risk of JRD or calcium oxalate stones but in determining the appropriate course of treatment.

"Juvenile Renal Dysplasia" or "JRD" as used herein refers to a group of hereditary renal disorders in canines and is also known as juvenile nephropathy. Clinical features of JRD include, without limitation, immature structures consisting of undifferentiated fetal cells or tissue types found in the kidney. On biopsy fetal glomeruli are noted with varying degrees of frequency (ranging from a few percent to greater than 75%). Proteinuria is not a component of the disease. Renal clearance abnormalities are consistent with those found in any dog with chronic renal failure independent of etiology (Picut, C A and R M Lewis, 1987: Vet Pathol. 24:I56-I63, 1987).

"Calcium oxalate stones" as used herein refer to crystalline masses composed of calcium oxalate that form in the urinary tract and deposit in the bladder. Calcium oxalate stones are thought to have a genetic component in some breeds of dogs and cats (The Merck Veterinary Manual (2006).)

The term "sample" as used herein refers to any fluid, cell or tissue sample from a dog which can be assayed for Cox2. DNA and protein samples may be collected by relatively noninvasive techniques, i.e., with minimal penetration into body tissues of the animals to be tested. Common noninvasive tissue sample collection methods may be used and include withdrawing buccal cells via cheek swabs and withdrawing blood samples. Accordingly, in one embodiment, the sample comprises, without limitation, serum, plasma, stool, buccal cells or urine.

It will be appreciated that because the Cox2 gene disclosed herein is substantially homologous to the Cox2 gene throughout the canine species, the nucleic acid sequences of the present application may be used to detect DNA mutations in other breeds as well. Accordingly, the term "dog" as used herein refers to any breed of dog including, without limitation, Shih tzus, Lhasa apsos, and Soft Coated Wheaten Terriers, Miniature schnauzers, Golden retriever, Tibetan spaniel, Flat coated retriever, King Charles Cavalier spaniel, Standard Poodle, Cairn terrier, Tietan terrier, Bull Mastiff, Boxers, Finnish Harriers, Rhodesian ridgeback, Flat coated retriever, Norwegian Elkhound, Bedlington Terriers, Havanese, Shetland sheepdog, Bernese Mountain dog, English Cocker spaniels, Portuguese water dogs, German shepherd dogs, Chow Chows, Alaskan Malamutes, Yorkshire terriers, Irish Red and White setter Airedale Terriers, Irish Wolfhounds, Keeshonds, Old English sheepdogs, Collies and any hybrid dog. "Hybrid dog" is a term applied to offspring from parents with purebred ancestry (example, Labradoodle, Cockapoo). Breeds most notably affected with JRD include Shih tzus, Lhasa apsos, and Soft Coated Wheaten Terriers and Miniature schnauzers.

The term "control" as used herein refers to a sample from an individual or a group of dogs who do not have JRD and/or calcium oxalate stones.

(i) Nucleic Acids

Accordingly, in an aspect of the disclosure, the inventor provides a method of detecting, monitoring or diagnosing JRD or calcium oxalate stones or a risk of JRD or calcium oxalate stones in a dog comprising detecting the presence of an allelic variant in the 5'UTR of Cox2 in a sample from the dog, wherein the presence of the variant is indicative of JRD or calcium oxalate stones or a risk of JRD or calcium oxalate stones in the dog. In one embodiment, the method is detecting, monitoring or diagnosing JRD or a risk of JRD. In another embodiment, the method is detecting, monitoring or diagnosing calcium oxalate stones.

In one embodiment, the allelic variant in the 5'UTR of Cox2 comprises a deletion or insertion. In an embodiment, the allelic variant in the 5'UTR of Cox2 comprises a deletion of 6 nucleotides starting at position-73 and a deletion of 11 nucleotides starting at position-37 of the canine Cox2 gene. In another embodiment, the allelic variant in the 5'UTR of Cox2 comprises a deletion of 6 nucleotides starting at position-68 and a deletion of 11 nucleotides starting at position-37 of the canine Cox2 gene. In another embodiment, the allelic variant in the 5'UTR of Cox2 comprises an insertion of 12 nucleotides starting at position-78 of the canine Cox2 gene. In one embodiment, the insertion comprises the nucleotide sequence CGCCTCCGCCTC (SEQ ID NO:31). In yet another embodiment, the allelic variant in the 5'UTR of Cox2 comprises an insertion of 24 nucleotides at position-78 of the canine Cox2 gene. In an embodiment, the insertion comprises the nucleotide sequence CGCCTCCGCCTCCGCCTCCGC-CGC (SEQ ID NO:32). In yet another embodiment, the allelic variant in the 5'UTR of Cox2 comprises a deletion of 6 nucleotides starting at position-73 of the canine Cox2 gene. In yet another embodiment, the allelic variant in the 5'UTR of Cox2 comprises a deletion of 6 nucleotides starting at position-68 of the canine Cox2 gene.

In another embodiment, the allelic variant in the 5'UTR of Cox2 comprises a single nucleotide polymorphism (SNP). In one embodiment, the allelic variant in the 5'UTR of Cox2 comprises a SNP at position-42 of the canine Cox2 gene. In an embodiment, the allelic variant in the 5'UTR of Cox2 comprises a C nucleotide at position-42 of the canine Cox2 gene.

In a further embodiment, the allelic variant in the 5'UTR of Cox2 comprises the nucleotide sequence as shown in SEQ ID NO:1, 2, 3 or 4.

It is well appreciated that regulatory DNA sequences, consisting of binding sites for transcription factors reside in the 5' untranslated regions of genes. In the present application, mutant alleles are described that interrupt (either by insertion or deletion of small regions of DNA) the promoter region, and are therefore likely to alter the transcription rate, and ultimately affect the amount of Cox2 protein produced. Presumably, since the mouse knockout model essentially constitutes a null mutation for the mouse Cox2 gene and results in a phenotype that is similar to the canine JRD model, it is likely that the changes in the promoter region of the canine Cox2 results in reduced amounts of Cox2 protein. Further, an artificial animal model of calcium oxalate urolithiasis was created by feeding rats Cox2 inhibitors along with sodium oxalate (Byong Chang Jeong; Min Young Park; Kwak Cheol; Bong Sub Kim; Kim Jung-In; Hyeon Hoe Kim 0.2005, Urological research, vol. 33, no6, pp. 453-459) and Example 2 shows that allelic variant 3 and allelic variant 1 of the canine Cox2 gene is associated with calcium oxalate stones. Thus, it is predicted that the levels of the Cox2 protein are decreased by allelic variants described as the rat model for calcium oxalate stone formation involves the use of Cox2 inhibitors.

Accordingly, in another embodiment, the inventor provides a method of detecting, monitoring or diagnosing JRD or calcium oxalate stones or a risk of JRD or calcium oxalate stones in a dog comprising detecting the level of expression of Cox2 in a sample from the dog compared to a control, wherein a change in expression compared to a control is indicative of JRD or calcium oxalate stones or a risk of JRD or calcium oxalate stones. In an embodiment, the change of expression is an increase in expression of Cox2. In another embodiment, the change of expression is a decrease in expression of Cox2. In one embodiment, the method is for detecting, monitoring or diagnosing JRD. In another embodiment, the method is for detecting, monitoring or diagnosing calcium oxalate stones.

The phrase "detecting, monitoring or diagnosing JRD" as used herein refers to a method or process of determining if a dog has or does not have juvenile renal dysplasia, or has or does not have an increased risk of developing JRD. Detection of differentially expressed Cox2 compared to a control or the presence of an allelic variant of Cox2, for example, in the 5'UTR, is indicative that the dog has JRD or an increased risk of developing JRD.

The phrase "detecting, monitoring or diagnosing calcium oxalate stones" as used herein refers to a method or process of determining if a dog has or does not have calcium oxalate stones, or has or does not have a risk of developing calcium oxalate stones. Detection of differentially expressed Cox2 compared to a control or the presence of an allelic variant of Cox2, for example, in the 5'UTR, is indicative that the dog has calcium oxalate stones or an increased risk of developing calcium oxalate stones.

The term "an increased risk" as used herein is an increased risk relative to a control sample.

The above described nucleic acid molecules allow those skilled in the art to construct nucleotide probes for use in the detection of nucleotide sequences homologous to canine Cox2 (SEQ ID NOs:5-12) and the allelic variants (SEQ ID NOs:1, 2, 3 or 4) or fragments thereof in a sample.

Accordingly, there is provided a method of detecting the presence or a change in the amount of nucleic acid molecule in a sample comprising contacting the sample under hybridization conditions with one or more nucleotide probes which hybridize to the nucleic acid molecules and are labelled with a detectable marker, and, optionally, determining the degree of hybridization between the nucleic acid molecule in the sample and the nucleotide probe(s).

In one embodiment, the nucleotide probe hybridizes to SEQ ID NOs:5-12 and the amount of hybridization is determined to indicate the level of Cox2 expression. In another embodiment, the nucleotide probe hybridizes to SEQ ID NOs:1, 2, 3 or 4 and the detection of hybridization indicates the presence of an allelic variant of Cox2.

A person skilled in the art will appreciate that a number of methods can be used to measure or detect the level of RNA products within a sample, including microarrays, RT-PCR (including quantitative RT-PCR), nuclease protection assays and northern blots.

A nucleotide probe may be labelled with a detectable marker such as a radioactive label which provides for an adequate signal and has sufficient half life such as 32P, 3H, 14C or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Hybridization conditions which may be used in methods of the disclosure are described above and are known in the art and are also described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

The term "change in expression of Cox2 in the sample from the dog as compared to the control" means that Cox2 is differentially expressed in the sample from the subject as compared to the control.

The term "differentially expressed" or "differential expression" as used herein refers to a difference in the level of expression of Cox2. The term "difference in the level of expression" refers to an increase or decrease in the measurable expression level of Cox2 as compared with the measurable expression level of Cox2 in a second sample or control. The term can also refer to an increase or decrease in the measurable expression level of Cox2 in a population of samples as compared with the measurable expression level of Cox2 in a second population of samples. In one embodiment, the differential expression can be compared using the ratio of the level of expression of Cox2 as compared with the expression level of the Cox2 of a control, wherein the ratio is not equal to 1.0. For example, a protein is differentially expressed if the ratio of the level of expression in a first sample as compared with a second sample is greater than or less than 1.0. For example, a ratio of greater than 1, 1.2, 1.5, 1.7, 2, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, Cox2 is identified as being differentially expressed as between a first and second population when the p-value is less than 0.1, preferably less than 0.05, more preferably less than 0.01, even more preferably less than 0.005, the most preferably less than 0.001.

A nucleic acid molecule of the disclosure also permits the identification and isolation, or synthesis of nucleotide sequences which may be used as primers to amplify a nucleic acid molecule of the disclosure, for example, in a polymerase chain reaction (PCR) which is discussed in more detail below. Examples of primers are shown in Table 1 and below.

Detection of the presence of allelic variants in the Cox2 promoter can be accomplished by a variety of methods, including, but not limited to nucleic acid amplification, such as polymerase chain reaction amplification (PCR), hybridization with allele-specific oligonucleotides such as molecular beacons (Tyagi S and Kramer F R (1996) Molecular beacons: probes that fluoresce upon hybridization. Nat Biotechnol 14, 303-308), allele specific ligation chain reaction (LCR), and radioactive and/or fluorescent DNA sequencing procedures well known in the art.

"Nucleic acid amplification" or "amplify" as used herein refers to a process by which nucleic acid sequences are amplified in number. There are several means known to those skilled in the art for amplifying nucleic acid sequences including, without limitation, polymerase chain reaction ("PCR"), ligase chain reaction (LCR), and nucleic acid sequence-based amplification (NASBA).

Pairs of primers may be selected wherein one primer is upstream of the site of insertion or deletion of the specific allelic variant of Cox2 and one primer is downstream of the site of insertion or deletion of the specific allelic variant of Cox2. Accordingly, in an embodiment, primers that are able to amplify a region of the 5'UTR of canine Cox2 are used. In another embodiment, the region of the 5'UTR comprises SEQ ID NO:1, 2, 3, 4 or 5.

In yet another embodiment, one primer is upstream of position-78 and a one primer is downstream of position-37 of the 5'UTR of canine Cox2 as shown in SEQ ID NO:1, 2, 3, 4 or 5.

In a particular embodiment, there is provided:

```
                                          (SEQ ID NO: 13)
a forward primer,
5'- ACA GCG CCT GCC TCC TCC A -3';
and (SEQ ID NO: 14)
a reverse primer,
5'- AGG TAC CCA CCT GCG CGG ACG A -3'.
```

In one embodiment, the method of detection of mutant JRD or calcium oxalate stone alleles is performed by PCR, and the allelic discrimination is determined by separation of amplified products by gel electrophoresis, and thus molecular weight. One skilled in the art can appreciate that primer designations surrounding the Cox2 mutant alleles is arbitrary, and other PCR primer sequences can be used to amplify the regions surrounding the mutation described within. Further these amplification products can be analyzed by standard methods such as electrophoretic separation and detection using ethidium bromide, or other suitable detection method, including isolation of these PCR products and DNA sequencing. In a particular embodiment, primers as shown in Table 1 (SEQ ID NOs:15-30) can be used to amplify the various regions of the Cox2 gene.

The length and bases of primers for use in a PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the disclosure are oligonucleotides, i.e., molecules containing two or more deoxyribonucleotides of the nucleic acid molecule of the disclosure which occur naturally as in a purified restriction endonuclease digest or are produced synthetically using techniques known in the art such as for example phosphotriester and phosphodiester methods (See Good et al. Nucl. Acid Res 4:2157, 1977) or automated techniques (See for example, Conolly, B. A. Nucleic Acids Res. 15:15(7): 3131, 1987). The primers are capable of acting as a point of initiation of synthesis when placed under conditions which permit the synthesis of a primer extension product which is complementary to a DNA sequence of the disclosure, i.e., in the presence of nucleotide substrates, an agent for polymerization such as DNA polymerase and at suitable temperature and pH. Preferably, the primers are sequences that do not form secondary structures by base pairing with other copies of the primer or sequences that form a hairpin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the disclosure or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the disclosure a method of determining the presence of an allelic variant of the disclosure or a change in expression of Cox2 is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

Polymerase chain reaction as used herein refers to a process for amplifying a target nucleic acid sequence as generally described in Innis et al, Academic Press, 1990 in Mullis et al., U.S. Pat. No. 4,863,195 and Mullis, U.S. Pat. No. 4,683,202. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3-12, Academic Press 1989.

The amplified products can be isolated and distinguished based on their respective sizes using techniques known in the art. For example, after amplification, a DNA sample can be separated on an agarose gel and visualized, after staining with ethidium bromide, under ultra violet (uv) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction enzyme digestion and electrophoretic separation or other techniques known in the art.

Conditions which may be employed in the methods of the disclosure using PCR are those which permit hybridization and amplification reactions to proceed in the presence of DNA in a sample and appropriate complementary hybridization primers. Conditions suitable for a polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp 3-12, Academic Press 1989. To amplify DNA template strands, preferably, the PCR utilizes polymerase obtained from the thermophilic bacterium Thermus aquatics (Taq polymerase, GeneAmp Kit, Perkin Elmer Cetus) or other thermostable polymerase.

(ii) Binding Proteins

In another embodiment, the disclosure provides a method of detecting, monitoring or diagnosing JRD or calcium oxalate stones or a risk of JRD or calcium oxalate stones in a dog comprising the steps of:
  (a) contacting a sample of said dog with a binding protein specific for Cox2;
  (b) measuring the amount of the binding protein-protein complex in the sample; and
  (c) comparing the amount of binding protein-protein complex in the sample to a control;
    wherein a change in the amount of binding protein-protein complex in the sample as compared to control is indicative of JRD or calcium oxalate stones or a risk of JRD or calcium oxalate stones. In one embodiment, the method is detecting, diagnosing or monitoring JRD or a risk of JRD. In another embodiment, the method is detecting, diagnosing or monitoring calcium oxalate stones or a risk of calcium oxalate stones.

The phrase "binding protein specific for Cox2" as used herein refers to a binding protein such as an isolated protein, that specifically binds a canine Cox2 protein.

In one embodiment, the amount of binding protein-protein complex in the sample is increased compared to control. In another embodiment, the amount of binding protein-protein complex in the sample is decreased compared to control.

In one embodiment, the binding protein used in the above method is an antibody that binds an antigen to form an antibody-antigen complex. The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')$_2$, scFv, dsFv, ds-scFv, dimers, minibodies, diabodies, and multimers thereof, multispecific antibody fragments and domain antibodies. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Conventional methods can be used to prepare the antibodies. For example, by using a peptide of a canine Cox2 protein, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal with the antigen of interest (e.g. Cox2) and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the antigen of interest and the monoclonal antibodies can be isolated.

The antibodies may be labelled with a detectable marker including various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I-131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

In another embodiment, the detectable signal is detectable indirectly. For example, using a labeled secondary antibody.

Antibodies reactive against Cox2 proteins may be used to detect Cox2 protein in various samples, for example they may be used in any known immunoassays which rely on the binding interaction between an antigenic determinant of Cox2 and the antibodies. Antibodies to canine Cox2 are described in the art (Assessment of Cyclooxygenase-2 Expression in Canine Hemangiosarcoma, Histiocytic Sarcoma, and Mast Cell Tumor, D. A. Heller, C. A. Clifford, M. H. Goldschmidt, D. E. Holt, M. J. Manfredi and K. U. Sorenmo Vet Pathol 42:350-353 (2005); U.S. Pat. No. 7,476,524 Wisnewski, et al. Jan. 13, 2009: Canine COX-2 nucleic acid molecules).

Examples of such assays are radioimmunoassays, western immunoblotting, enzyme immunoassays (e.g., ELISA), immunofluorescence, immunoprecipitation, latex agglutination, hemagglutination, and histochemical tests. Thus, the antibodies may be used to identify or quantify the amount of a protein in a sample.

In a method of the application, a predetermined amount of a sample or concentrated sample is mixed with antibody or labelled antibody. The amount of antibody used in the method is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the disclosure is separated from the unreacted antibody by washing with a buffer, for example, phosphate buffered saline (PBS) with bovine serum albumin (BSA).

When labelled antibody is used, the level of Cox2 protein can be determined by measuring the amount of labelled antibody bound to a protein of the disclosure in the sample or of the unreacted labelled antibody. The appropriate method of measuring the labelled material is dependent upon the labelling agent.

When unlabelled antibody is used in a method, the level of Cox2 can be determined by measuring the amount of antibody bound to the Cox2 using substances that interact specifically with the antibody to cause agglutination or precipitation. In particular, labeled antibody against an antibody specific for a protein, can be added to the reaction mixture. The antibody against an antibody specific for a protein of the disclosure can be prepared and labeled by conventional procedures known in the art which have been described herein.

The antibody against an antibody specific for a protein of the disclosure may be a species specific anti-immunoglobulin antibody or monoclonal antibody, for example, goat anti-rabbit antibody may be used to detect rabbit antibody specific for Cox2.

Any of the methods of the disclosure to diagnose, detect or monitor JRD or calcium oxalate stones or a risk of JRD or calcium oxalate stones can be used in addition or in combination with traditional diagnostic techniques for JRD or calcium oxalate stones. Typical methods to detect JRD include blood chemistry analysis indicative of abnormal renal function, and urinalysis which can be caused by any number of kidney diseases. Absolute confirmation of JRD is by an invasive wedge biopsy of the kidney which most breeders and owners are reluctant to do on an animal that is faced with chronic renal failure. As such the present invention can by used by veterinarians to confirm JRD as the diagnosis in conjunction with standard kidney function tests.

Conventional diagnosis of calcium oxalate stones is by x-rays or ultrasound, however the mass itself must be identified by its chemical composition. The optimal management of the genetic component of this disease is to eliminate risk factors (mutations) from breeding populations to reduce the tendency for individuals to develop these stones.

In addition, allelic variants or altered Cox2 expression found in dogs may represent other disease abnormalities like those found in the Cox2 knockout mouse, in particular, patent ductus arteriosus or female infertility. One skilled in the art can appreciate that detection of the allelic variants or altered expression of the Cox2 gene may be useful to identify other disease processes within canine breeds.

The diagnostic methods of the present application may be used to determine the Cox2 genotype of an individual dog, or a set of dogs that are closely related to a dog known to be affected with JRD or calcium oxalate stones, by identifying in each of these dogs which alleles are present using a set by virtue of their molecular weight.

Breeding Methods

The methods of the present application provide an accurate test for distinguishing non-carriers, homozygous carriers and heterozygous carriers of the defective Cox2 alleles by virtue of their molecular weight.

Overall, the present application provides breeders with an accurate, definitive test whereby the undesired Cox2 gene may be eliminated from breeding lines. Accordingly, in a further aspect, there is provided a method of producing dogs that have a reduction in JRD risk or calcium oxalate stone risk, comprising the steps:
  (a) genotyping male and female dogs for the presence of an allelic variant of Cox2;
  (b) selecting a male and female dog that do not have the allelic variants of Cox2; and
  (c) mating the dogs of step (b) to produce offspring that do not have an allelic variant of Cox2;

wherein the absence of an allelic variant of Cox2 provides a reduction in JRD risk or calcium oxalate stone risk. In an embodiment, the method is for producing dogs that have a reduction in JRD risk. In another embodiment, the method is for producing dogs that have a reduction in calcium oxalate stones.

One skilled in the art will appreciate that this method can be applied to any breed that is afflicted with JRD or calcium oxalate stones. Since JRD is inherited as an autosomal dominant trait with incomplete penetrance, any hybrid dog (crossbred) with a parent from a breed that has the JRD mutation can pass it onto its progeny. JRD, a dominant mutation, is found in such high frequency in so many breeds that are used to generate hybrids that as a practical matter, spread of JRD to progeny from hybrid crosses is unpreventable. So far, the frequency of the JRD mutation is high in every breed that the present inventor has studied with the exception of the German Shepherd dog. Therefore, the methods described herein are also applicable to cross bred dogs, and even mixed breeds.

Kits

A further aspect of the disclosure is a kit for diagnosing, detecting or monitoring JRD or calcium oxalate stones or a risk of JRD or calcium oxalate stones comprising any one of the binding proteins of the disclosure. In one embodiment, the kit further comprises instructions for use. In another embodiment of the disclosure, the binding protein is an antibody. In yet another embodiment, the binding protein is labeled using a detectable marker.

In yet another aspect is a kit for diagnosing, detecting or monitoring JRD or calcium oxalate stones or a risk of JRD or calcium oxalate stones comprising any one of the primers or probes of the disclosure. In one embodiment, the kit further comprises instructions for use. In another embodiment, the primer or probe is labeled using a detectable marker.

The kits of the present application may further comprise at least one additional reagent such as a lysing buffer for lysing cells contained in the specimen; enzyme amplification reaction components dNTPs, reaction buffer, and amplifying enzyme; or a combination of the additional reagents. In one embodiment, the kits described herein are for diagnosing, detecting or monitoring JRD or a risk of JRD. In another embodiment, the kits described herein are for diagnosing, detecting or monitoring calcium oxalate stones or a risk of calcium oxalate stones.

Method of Screening for Additional Genetic Markers of JRD

Genetic markers can be made using different methodologies known to those in the art. For example, the Cox2 gene of canine chromosome 7 may be microdissected, and fragments cloned into vectors to isolate DNA segments which can be tested for linkage with the Cox2 gene locus. Alternatively, isolated DNA segments can be obtained from the Cox2 locus of canine chromosome 7 by nucleic acid amplification (e.g., polymerase chain reaction) or by nucleotide sequencing of the relevant region of chromosome 7 ("chromosome walking"). Using a linkage test, the DNA segments may be assessed for their ability to co-segregate with the Cox2 gene locus, and thus determine the usefulness of each DNA segment in a molecular diagnostic assay for detection of Cox2 or the carrier status.

The "locus" of a genetic marker or marker as used herein refers to its situ on the chromosome in relation to another locus.

The term "genetic marker indicative of a mutation in the Cox2 gene locus" refers to a marker that: (a) is genetically linked and co-segregates with the Cox2 gene locus; (b) comprises a region of canine chromosome encompassing the canine Cox2 gene both coding and non-coding sequences (c) contains a polymorphism informative for the Cox2 genotype; and (d) can be used in a linkage assay or other molecular diagnostic assay (DNA test) to identify normal alleles (wild type; (+)), and mutant (Cox2) alleles (−) (by the presence of the polymorphism), and hence can distinguish Cox2, Cox2 carriers dogs (+/−), and those with two copies of mutations (−/−), and those that are normal (+/+).

In that regard, markers additional to those illustrative examples disclosed herein, that map either by linkage or by physical methods so close to the Cox2 gene locus that any polymorphism in or with such derivative chromosomal regions, may be used in a molecular diagnostic assay for detection of JRD or calcium oxalate stones or the carrier status.

"Co-segregate" as used herein refers to inheritance together of two specific loci, e.g., the loci are located so physically close on the same chromosome that the rate of genetic recombination between the loci is as low as 0%, as observed by statistical analysis of inheritance patterns of alleles in a mating.

"Linkage" as used herein refers to co-segregation of two loci in the canine breed analyzed.

"Linkage test" and "molecular diagnostic assay" as used herein refer to a method for determining the presence or absence of one or more allelic variants linked with the Cox2 gene locus, such that the method may be used for the detection of JRD or calcium oxalate stones or carrier status, whether through statistical probability or by actual detection of a mutated Cox2 gene.

"Polymorphism" as used herein refers to a marker that is distinguishably different including, without limitation, by size, electrophoretic migration, nucleotide sequence, ability to specifically hybridize to an oligonucleotide under standard conditions) as compared to an analogous region from a dog of the same breed or pedigree.

With the knowledge demonstrated herein that DNA sequences (polymorphic markers) of canine chromosome 7 have been identified as being linked to the Cox2 locus, additional markers may be generated from the known sequences or indicated location on canine chromosome 7.

FIGS. 1 and 3 show the sequences of various introns and exons of the canine Cox2 gene (SEQ ID NOs:5-12). In each sequence, exons are shown in upper case letters, while introns are shown in lower case.

It will be appreciated by those skilled in the art that the alleles that make up the genotypes of the genetic markers in the canine population (or within a specific breed of dog, or within a specific family of dogs) may vary by a single base pair or limited number of base pair substitutions in the DNA, or the differences may comprise many base pairs as seen in a transversion. Nevertheless, analysis of a pedigree with the genetic marker using the methods according to the present application may be sufficient to establish that the genetic marker may be used for that pedigree in detecting a mutation in the Cox2 gene locus.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

The disclosed nucleic acid sequences represent the canine Cox2 gene, and allelic variations thereof. DNA sequences presented from a clinical sample from a standard Poodle and a miniature schnauzer show that the coding sequences of the canine Cox2 are 100% agreement with the public domain assembled canine genome.

Table 1 shows the PCR primers used to amplify the various regions of the canine Cox2 gene. The primers in table 1 amplify a larger fragment than the diagnostic primers described above for ease of separation on electrophoresis.

Mode of Inheritance. Determined as Dominant with Incomplete Penetrance

Example 1

Soft Coated Wheaten Terriers (SCWTs)

In this example, two SCWT's that were bred were homozygous for mutant alleles. The sire was homozygous for mutant allele 3 and the dam was heterozygous for mutant alleles two and three. Therefore all of the offspring would have two mutant alleles. In one breeding by this sire a JRD puppy was diagnosed at 4 months. The diagnosis was by biopsy, blood work, ultrasound and ultimately autopsy. Thirty six offspring in total were produced by this male with seven different partners, thus demonstrating the apparent low level of penetrance. This was the only breeding for this dam.

In another case a SCWT female that was homozygous for mutant allele 3 and bred only once produced a litter of seven with one JRD clinical puppy. JRD in this case was determined by autopsy. Again irrespective of the genotype of the sire, all of the puppies would have at least one copy of allele 3. One of the siblings to the JRD affected puppy was tested as homozygous mutant allele. Therefore the sire of this litter also had a mutant allele 3 chromosome.

In the final example, a female that was homozygous for mutant alleles 2 and 3 was bred with a sire that was clear (wild type). Therefore, all of the offspring would have one copy of a mutant allele. One of the puppies in this litter was diagnosed with JRD by autopsy. The sire, who was clear had produced 11 litters, prior to this one with no JRD puppies reported. This example shows that carriers can develop JRD, while in this first example above animals that were homozygous for the mutant allele developed JRD.

Not all animals that have the mutation (one or two copies), however, develop this disease. Thus, the mode of inheritance is shown to be dominant with incomplete penetrance.

Lhasa Apsos

In this example a sire that was heterozygous for alleles 2 and 3 was bred to a female that was biopsy positive and the genotype was not determined, but by extrapolation the dam had at least one mutant allele as one of the puppies was heterozygous for mutant allele 2 and 3. This was the only puppy that was genotyped. This particular puppy had 40% fetal glomeruli on biopsy, however, lived a normal life with no clinical signs of kidney disease. All 5 puppies were biopsy positive in this example: puppy 1) 10% fetal glomeruli, puppy 2) 15% fetal glomeruli, puppy 3) was the above mentioned puppy with 40% fetal glomeruli, Puppy 4) 4% fetal glomeruli and puppy 5) 15% fetal glomeruli. None of these puppies had kidney function problems.

In another example, the same sire was bred to another female, and produced a puppy that supposedly had JRD and died of complications of renal failure at 5 months. A liitermate to this puppy biopsied with 10% fetal glomeruli, although again was able to concentrate urine normally.

Shih Tzu

In this example, a male that was a carrier of mutant allele 1 was bred to a clear female. One puppy out of five was diagnosed with JRD by biopsy, and was shown to be a carrier. The genotype of the rest of the litter was not determined.

Given the mode of inheritance, a specific DNA-based genetic test is necessary for disease management in many canine breeds. Diagnosis of breeds affected with JRD by wedge biopsy, an invasive procedure until the development of this test was the best tool to attempt to manage this disease, however, even with this, biopsy negative animals have been shown to produce JRD affected progeny.

Table 2 below shows the relationship of clinical data with allelic variants in the 5' UTR of the canine Cox2.

Example 2

Calcium Oxalate Stones

Eight Yorkshire terriers and one Standard Poodle diagnosed with calcium oxalate stones were examined for the JRD mutation. All of the samples submitted had allele variant 3. The Poodle was a carrier. Four of the Yorkshire terriers were homozygous for allele variant 3, three were carriers of allele 3, and one was heterozygous for allele 1 and allele 3. The main allelic variant in Standard Poodles is allele 2. Therefore, it is conceivable that the majority of calcium oxalate stones in these breeds could be associated with allelic variation 3.

Four miniature schnauzers dogs that had calcium oxalate stones removed tested as homozygous for allelic variant 1. One of these also had JRD that was diagnosed by ultrasound.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| REGION OF GENE | FORWARD PRIMER 5'-3' | REVERSE PRIMER 5'-3' |
| --- | --- | --- |
| 5'UTR-exon1-part of intron1 | 5'- TTG TCA AAC AAC TTG CAG CGA GCG -3' (SEQ ID NO: 15) | 5'- ATC ACC CAG CCG AGG AGT C -3' (SEQ ID NO: 16) |
| Exons 2 and 3 and flanks | 5'- CCT GGT TGA ACG TTG TTG GCC TTA -3' (SEQ ID NO: 17) | 5'- CCC ACT CAG GTT CAT TCT CTC A -3' (SEQ ID NO: 18) |
| Exon 4 and flanks | 5'- CCA TGG ACC ACT GGT TTA CAA TAG G -3' (SEQ ID NO: 19) | 5'- GAG ATT CAC AGA TAT CCT CAA GCA -3' (SEQ ID NO: 20) |

TABLE 1-continued

| REGION OF GENE | FORWARD PRIMER 5'-3' | REVERSE PRIMER 5'-3' |
|---|---|---|
| Exon 5 and flanks | 5'- CTC CTG TAA GTG AAG AAA GCC C -3' (SEQ ID NO: 21) | 5'- ATG CGT GTG TGT GCT TGA GT -3' (SEQ ID NO: 22) |
| Exon 6 and 7 and flanks | 5'- ACT ATT TAG TGG TTG TGA GAG AAA CG -3' (SEQ ID NO: 23) | 5'- AGT AAC ATG CCA GCT TTC TCT GGG -3' (SEQ ID NO: 24) |
| Exon 8 and flanks | 5'- ACA AGA TTG CAT TTC AGT TGC TTG -3' (SEQ ID NO: 25) | 5'- CAG AAA GAT CAC TTT GGT GGC AGA -3' (SEQ ID NO: 26) |
| Part of Exon 9 intron 9 and part of exon 10 | 5'- GCA TTA GTC TTC CCT CCT TTG TAC CC -3' (SEQ ID NO: 27) | 5'- ACC ATG GTC TCA CCA AAG ATG GCA -3' (SEQ ID NO: 28) |
| EXON 10 and flanks | 5'- GTT GAA AGG GAA TTG AGC AAA GGG -3' (SEQ ID NO: 29) | 5'- CAG GCT TCT ATA GTT CAG TTG ACC G -3' (SEQ ID NO: 30) |

TABLE 2

| ANIMAL NUMBER | BREED | DIAGNOSIS | GENOTYPE | Comments |
|---|---|---|---|---|
| 1 | LHASA APSO | Biopsy+ | ALLELE2/ALLELE3 | 40% fetal glomeruli, lived normal life, with ability to concentrate urine normal |
| 2 | LHASA APSO | Biopsy+ | ALLELE3/WT | 25% fetal glomeruli-not clinical |
| 3 | LHASA APSO | Biopsy+ | ALLELE2/ALLELE3 | 5% fetal glomeruli: produced JRD litter/ bred to carrier of ALLELE2 |
| 4 | LHASA APSO | Biopsy+ | ALLELE2/ALLELE2 | 3%-5% fetal glomeruli: |
| 5 | LHASA APSO | Biopsy- | ALLELE2/WT | BRED TO BIOPSY NEGATIVE: PRODUCED BIOPSY + OFFSPRING |
| 6 | LHASA APSO | Biopsy Normal | WT/WT | |
| 7 | LHASA APSO | Biopsy Normal | WT/WT | |
| 8 | LHASA APSO | Biopsy Normal | WT/WT | |
| 9 | LHASA APSO | Biopsy Normal | ALLELE3/WT | |
| 10 | POODLE | Biopsy+ | ALLELE2/WT | Deceased from JRD 75% fetal glomeruli |
| 11 | POODLE | Biopsy+ | ALLELE2/ALLELE2 | 17% Fetal glomeruli |
| 12 | POODLE | Biopsy+ | ALLELE2/WT | 5% Fetal glomeruli |
| 13 | GOLDEN RETREIVER | Blood Biochemistry/Urinalysis | ALLELE3/WT | Deceased from JRD <1 yr. |
| 14 | SHIH TZU | Uninalysis showed low specific gravity | ALLELE1/WT | Deceased from JRD <6 months |
| 15 | SHIH TZU | Biopsy+ | ALLELE1/WT | Deceased from JRD <6 months |
| 16 | SHIH TZU | Uninalysis showed low specific gravity | ALLELE1/ALLELE1 | Deceased from JRD |
| 17 | SHIH TZU | Uninalysis showed low specific | ALLELE1/WT | Deceased from JRD <6 months |

TABLE 2-continued

| ANIMAL NUMBER | BREED | DIAGNOSIS | GENOTYPE | Comments |
|---|---|---|---|---|
| 18 | SHIH TZU | Uninalysis showed low specific | ALLELE1/WT | |
| 19 | GORDON SETTER | Biopsy+ | ALLELE1/WT | Deceased from JRD |
| 20 | TIBETAN TERRIER | Autopsy | ALLELE1/WT | Deceased from JRD |
| 21 | ENGLISH COCKER SPANIEL | Biopsy+ | ALLELE1/ ALLELE1 | Deceased from JRD |
| 22 | BOXER | Ultrasound | ALLELE3/WT | Deceased from JRD |
| 23 | WEIMARINER | Blood Biochemistry/ Urinalysis | ALLELE2/ ALLELE2 | Deceased from JRD |
| 24 | BERNESE MOUNTAIN DOG | Autopsy | ALLELE3 (carrier or homozygote) | Progeny (2) - one was carrier allele, and one homozygote allele 3 |

The invention claimed is:

1. A method of genotyping a dog to detect the presence of an allelic variant in the 5'UTR of Cox2 comprising:
   (a) providing a sample containing DNA from a dog;
   (b) contacting DNA from the sample with a PCR primers comprising SEQ ID NO:13 and SEQ ID NO:14;
   (c) detecting the allelic variant of (i) a deletion of 6 nucleotides starting at position −68/−73 and a deletion of 11 nucleotides starting at position −37 of the canine Cox2 gene; (ii) an insertion of 12 nucleotides at position −78 of the canine Cox2 gene, wherein the insertion comprises the nucleotide sequence CGCCTCCGCCTC (SEQ ID NO:31);
   and/or (iii) an insertion of 24 nucleotides at position −78 of the canine Cox2 gene, wherein the insertion comprises the nucleotide sequence CGCCTCCGCCTCCGCCTC-CGCCGC (SEQ ID NO:32);
   wherein detecting the allelic variant comprises amplifying the nucleotide sequence using the PCR primers; and
   (d) identifying the dog as having the allelic variant in the 5'UTR of Cox2.

2. The method of claim 1, wherein the allelic variant detected in step (c) comprises the nucleotide sequence of SEQ ID NO:1, 2 or 3.

3. The method of claim 1, wherein providing a sample containing DNA from a dog comprises withdrawing buccal cells or withdrawing a blood sample.

4. The method of claim 1, further comprising identifying that the dog having the allelic variant in the 5' UTR of Cox2 is at an increased risk of juvenile renal dysplasia (JRD).

5. A method of genotyping a dog to detect the presence of an allelic variant in the 5'UTR of Cox2 comprising:
   (a) providing a sample containing DNA from a dog, wherein the dog is a Lhasa Apso or German Shepherd dog;
   (b) contacting DNA from the sample with PCR primers comprising SEQ ID NO:13 and SEQ ID NO:14;
   (c) detecting the allelic variant of:
   (i) a deletion of 6 nucleotides starting at position −68/−73 and a deletion of 11 nucleotides starting at position −37 of the canine Cox2 gene, wherein the dog is a German Shepherd dog; or
   (ii) an insertion of 12 nucleotides at position −78 of the canine Cox2 gene, wherein the insertion comprises the nucleotide sequence CGCCTCCGCCTC (SEQ ID NO:31) and/or an insertion of 24 nucleotides at position −78 of the canine Cox2 gene, wherein the insertion comprises the nucleotide sequence CGCCTCCGC-CTCCGCCTCCGCCGC (SEQ ID NO:32); wherein the dog is a Lhasa Apso dog;
   wherein detecting the allelic variant comprises amplifying the nucleotide sequence using the PCR primers; and
   (d) identifying the dog as having the allelic variant in the 5'UTR of Cox2.

* * * * *